US012344571B1

(12) United States Patent
Wang et al.

(10) Patent No.: US 12,344,571 B1
(45) Date of Patent: Jul. 1, 2025

(54) ORGANIC COLOR CENTER-TAILORED, SEMICONDUCTING CARBON NANOTUBES AND THEIR METHOD OF MANUFACTURE

(71) Applicant: University of Maryland, College Park, College Park, MD (US)

(72) Inventors: Yuhuang Wang, Laurel, MD (US); Hongbin Luo, College Park, MD (US); Peng Wang, Rockville, MD (US)

(73) Assignee: University of Maryland, College Park, College Park, MD (US)

( * ) Notice: Subject to any disclaimer, the term of this patent is extended or adjusted under 35 U.S.C. 154(b) by 0 days.

(21) Appl. No.: 17/365,924

(22) Filed: Jul. 1, 2021

Related U.S. Application Data

(60) Provisional application No. 63/217,645, filed on Jul. 1, 2021, provisional application No. 63/046,969, filed on Jul. 1, 2020.

(51) Int. Cl.
| | |
|---|---|
| *C07C 211/53* | (2006.01) |
| *C01B 32/159* | (2017.01) |
| *C01B 32/174* | (2017.01) |
| *C07C 209/68* | (2006.01) |
| *C09B 67/00* | (2006.01) |
| *C09K 11/06* | (2006.01) |

(52) U.S. Cl.
CPC .......... *C07C 211/53* (2013.01); *C01B 32/159* (2017.08); *C01B 32/174* (2017.08); *C07C 209/68* (2013.01); *C09B 68/22* (2013.01); *C09B 68/40* (2013.01); *C09K 11/06* (2013.01); *C01B 2202/02* (2013.01); *C01B 2202/28* (2013.01); *C01P 2002/82* (2013.01); *C01P 2002/84* (2013.01); *C01P 2004/04* (2013.01); *C01P 2006/60* (2013.01); *C07C 2604/00* (2017.05); *C09K 2211/1007* (2013.01)

(58) Field of Classification Search
CPC . C07C 211/53; C07C 209/68; C07C 2604/00; C09B 68/22; C09B 68/40; C09K 11/06; C09K 2211/1007; C01B 2202/02; C01B 2202/28; C01P 2002/82; C01P 2002/84; C01P 2004/04; C01P 2006/60
See application file for complete search history.

(56) References Cited

U.S. PATENT DOCUMENTS

| | | | |
|---|---|---|---|
| 6,864,501 B2 | 3/2005 | Shields et al. | |
| 7,141,727 B1 | 11/2006 | Appenzeller et al. | |
| 7,359,514 B2 | 4/2008 | Trifonov et al. | |
| 7,459,137 B2 * | 12/2008 | Tour ...................... | B82Y 40/00 |
| | | | 977/840 |
| 8,373,157 B2 | 2/2013 | Choi et al. | |
| 8,404,506 B2 | 3/2013 | Lochmann et al. | |
| 8,980,216 B2 | 3/2015 | Wang et al. | |
| 9,983,058 B2 | 5/2018 | Wang et al. | |
| 10,316,247 B2 | 6/2019 | Maki et al. | |
| 10,414,974 B2 | 9/2019 | Wang et al. | |
| 11,208,571 B2 | 12/2021 | Wang et al. | |
| 12,098,074 B1 * | 9/2024 | Wang ...................... | C01B 32/162 |
| 2006/0175601 A1 | 8/2006 | Lieber | |
| 2007/0280876 A1 * | 12/2007 | Tour ...................... | C01B 32/174 |
| | | | 423/460 |
| 2017/0192354 A1 | 7/2017 | Zhao | |
| 2017/0316487 A1 | 11/2017 | Mazed | |
| 2018/0265779 A1 * | 9/2018 | Wang ................. | C09K 11/0827 |
| 2019/0367806 A1 | 12/2019 | Han | |
| 2020/0013991 A1 | 1/2020 | Wang | |
| 2020/0048489 A1 * | 2/2020 | Wang ...................... | C01B 32/172 |

FOREIGN PATENT DOCUMENTS

| | | | | |
|---|---|---|---|---|
| EP | 1503328 | | 5/2007 | |
| WO | WO-03004741 A1 * | 1/2003 | ............. | B82Y 15/00 |
| WO | WO-2004007364 A1 * | 1/2004 | ............. | B82Y 10/00 |

OTHER PUBLICATIONS

M. Kim et al., 4 Chem, 2180-2102 (2018) (Year: 2018).*
Y. Piao et al., 5 Nature Chemistry, 840-845 (2013) (Year: 2013).*
M. Auffan et al., 4 Nature Nanotechnology, 634-641 (2009) (Year: 2009).*
S. Suarez et al., 114 Journal of Physical Chemistry B, 8941-8947 (2010) (Year: 2010).*
D. DesMarteau, 289 Science, 72-73 (2000) (Year: 2000).*
H. Luo et al., 13 ACS Nano, 8417-8424 (Jul. 3, 2019) (Year: 2019).*
J. Hudson et al., 126 Journal of the American Chemical Society, 11158-11159 (2004) (Year: 2004).*
P. Wang, Solution Processing of Long Carbon Nanotubes: From Fundamentals to Applications (Feb. 1, 2020) (Year: 2020).*
P. Wang et al., 144 Journal of the American Chemical Society, 13234-13241 (2022) (Year: 2022).*
J. Hudson et al., 18 Chemistry of Materials, 2766-2770 (2006) (Year: 2006).*

(Continued)

*Primary Examiner* — Alexander R Pagano
(74) *Attorney, Agent, or Firm* — Leydig, Voit & Mayer, Ltd.

(57) ABSTRACT

Organic color center-tailored carbon nanotubes, particularly semiconducting single-walled carbon nanotubes, are of significant interest for imaging, sensing, and quantum information processing applications. A high-yield, simple, one-pot synthetic route for producing these materials exceeding the current μg/mL scale is provided. Adding an acid solution of raw carbon nanotubes, nitrite, and an aniline derivative into a reactive solvent, such as water, results in covalently bonded organic color center-tailored nanotubes. No radical initiator or heating is required for the reaction. The chemistry works for all the nanotube chiralities investigated. The synthesized materials are neat solids that can be readily dispersed in either water or an organic solvent using a surfactant or polymer depending on the specific application. The OCC-products can also be further sorted into single chirality-enriched fractions with defect-specific photoluminescence that is tunable over approximately 1100 to approximately 1550 nm.

10 Claims, 19 Drawing Sheets

(56) References Cited

OTHER PUBLICATIONS

Assresahegn et al. (2015) "Advances on the use of diazonium chemistry for functionalization of materials used in energy storage systems," Carbon 92, 362-381.

Bahr et al. (2001) "Highly Functionalized Carbon Nanotubes Using in Situ Generated Diazonium Compounds," Chem. Mater. 13:3823-3824.

Biju (2014) "Chemical Modifications and Bioconjugate Reactions of Nanomaterials for Sensing, Imaging, Drug Delivery and Therapy," Chem. Soc. Rev., 43, 744-764.

Brozena et al. (Jun. 2019) "Controlling the Optical Properties of Carbon Nanotubes with Organic Color-Center Quantum Defects," Nat. Rev. Chem. 3, 375-392. DOI: 10.1038/s41570-019-0103-5.

Davis et al. (2009) "True Solutions of Single-Walled Carbon Nanotubes for Assembly into Macroscopic Materials," Nat. Nanotechnol. 4, 830-834.

Dyke et al. (2004) "Covalent Functionalization of Single-Walled Carbon Nanotubes for Materials Applications," J. Phys. Chem. A, 51, 11151-11159.

Gifford et al. (2018) "Exciton Localization and Optical Emission in Aryl-Functionalized Carbon Nanotubes," J. Phys. Chem. C. 122, 1828-1838.

Gifford et al. (Aug. 2020) "Controlling Defect-State Photophysics in Covalently Functionalized Single-Walled Carbon Nanotubes," Accounts of Chemical Research 53, 1791-1801.

Gifford et al. (Nov. 2019) "Mod(n-m,3) Dependence of Defect-State Emission Bands in Aryl-Functionalized Carbon Nanotubes," Nano Letters 19, 8503-8509.

Hartmann et al. (2015) "Photoluminescence Imaging of Solitary Dopant Sites in Covalently Doped Single-wall Carbon Nanotubes," Nanoscale 7, 20521-20530.

He et al. (2017) "Low-Temperature Single Carbon Nanotube Spectroscopy of sp3 Quantum Defects," ACS Nano 11, 10785-10796.

He et al. (2017) "Tunable Room-Temperature Single-Photon Emission at Telecom Wavelengths from sp3 Defects in Carbon Nanotubes," Nat. Photonics 11, 577-582.

He et al. (2018) "Carbon nanotubes as emerging quantum-light sources," Nature Materials 17, 663-670.

Hudson et al. (2004) "Water-soluble, Exfoliated, Nonroping Single-Wall Carbon Nanotubes," J. Am. Chem. Soc. 126, 11158-11159.

Kim et al. (2018) "Mapping Structure-Property Relationships of Organic Color Centers," Chem 4, 2180-2191.

Kwon et al. (2015) "Optical Probing of Local pH and Temperature in Complex Fluids with Covalently Functionalized, Semiconducting Carbon Nanotubes," J. Phys. Chem. C 119, 3733-3739.

Kwon et al. (2016) "Molecularly Tunable Fluorescent Quantum Defects," J. Am. Chem. Soc. 138, 6878-6885.

Luo et al. (Jul. 2019) "One-pot, Large-scale Synthesis of Organic Color Center-Tailored Semiconducting Carbon Nanotubes," ACS Nano, 13, 8417-8424; and its Supporting Information. https://doi.org/10.1021/acsnano.9b04087.

Maeda et al. (2016) "Tuning of the Photoluminescence and Up-Conversion Photoluminescence Properties of Single-Walled Carbon Nanotubes by Chemical Functionalization," Nanoscale 8, 16916-16921.

Paulus et al. (2013) "Covalent Electron Transfer Chemistry of Graphene with Diazonium Salts," Accounts of Chemical Research 46, 160-170.

Piao et al. (2013) "Brightening of Carbon Nanotube Photoluminescence through the Incorporation of sp3 Defects," Nat. Chem. 5, 840-845.

Saha et al. (2018) "Narrow-band Single-Photon Emission through Selective Aryl Functionalization of Zigzag Carbon Nanotubes," Nat. Chem. 10, 1089-1095.

Schmidt et al. (2009) "Mechanism of the Coupling of Diazonium to Single- Walled Carbon Nanotubes and Its Consequences," Chemistry—A European Journal 15, 2101-2110.

Shiraki et al. (2016) "Near Infrared Photoluminescence Modulation of Single-Walled Carbon Nanotubes Based on a Molecular Recognition Approach," Chem. Commun. 52, 12972-12975.

Shiraki et al. (2017) "Near Infrared Photoluminescence Modulation by Defect Site Design Using Aryl Isomers in Locally Functionalized Single-Walled Carbon Nanotubes," Chem. Commun. 53, 12544-12547.

Shiraki et al. (2018) "Multistep Wavelength Switching of Near-Infrared Photoluminescence Driven by Chemical Reactions at Local Doped Sites of Single-Walled Carbon Nanotubes," Chem. Eur. J. 24, 19162-19165.

Wang et al. (2017) "Superacid-Surfactant Exchange: Enabling Nondestructive Dispersion of Full-Length Carbon Nanotubes in Water," ACS Nano 11, 9231-9238.

Wang et al. (Jul. 2022) "Quantum Defects: What Pairs with the Aryl Group When Bonding to the sp2 Carbon Lattice of Single-Wall Carbon Nanotubes?" J. Am. Chem. Soc. 144, 29, 13234-13241. https://doi.org/10.1021/jacs.2c03846.

Wu et al. (2018) "Photochemical Creation of Fluorescent Quantum Defects in Semiconducting Carbon Nanotube Hosts," Angew. Chem. Int. Ed. Engl. 57, 648-653.

Avouris, P., M. Freitag, et al. (2008). "Carbon-nanotube photonics and optoelectronics." Nat. Photonics 2(6): 341-350.

Chen, J., V. Perebeinos, et al. (2005). "Bright Infrared Emission from Electrically Induced Excitons in Carbon Nanotubes." Science (Washington, DC, U. S.) 310(5751): 1171-1174.

Gordon, L., J. R. Weber, et al. (2013). "Quantum computing with defects." MRS Bull. 38(10): 802-807.

Khasminskaya, S. et al. (2016) "Fully integrated quantum photonic circuit with an electrically driven light source." Nat. Photon. 10, 727-732.

Kwon, H.J., M. Kim et al. (2019) "Probing Trions at Chemically Tailored Trapping Defects," ACS Cen. Sci. 5 (11): 1786-1794.

Lounis, B. and M. Orrit (2005). "Single-photon sources." Rep. Prog. Phys. 68(5): 1129-1179.

Mueller, T., M. Kinoshita, et al. (2010). "Efficient narrow-band light emission from a single carbon nanotube p-n diode." Nat. Nanotechnol. 5(1): 27-31.

Pyatkov, F. et al. (2016) "Cavity Enhanced light emission from electrically driven carbon nanotubes," Nature Photonics, 10, 420-427.

Xu, B., X. Wu, M. Kim, P. Wang and Y. Wang (2021) "Electroluminescence from 4-nitroaryl organic color centers in semiconducting single-wall carbon nanotubes." J. Appl. Physics 129, 044305.

Zorn, N. F., F. J. Berger, and J Zaumseil (May 2021) "Charge Transport in and Electroluminescence from sp3-Functionalized Carbon Nanotube Networks," ACS Nano, 15, 6, 10451-10463.

\* cited by examiner

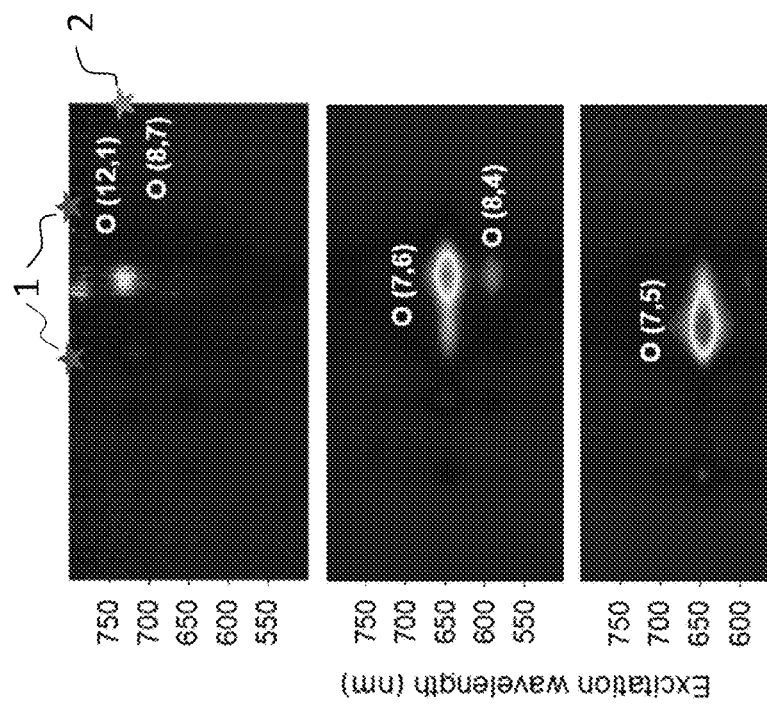
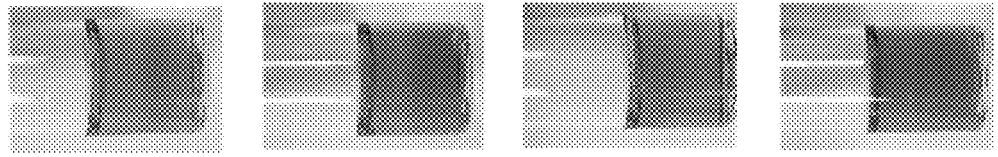
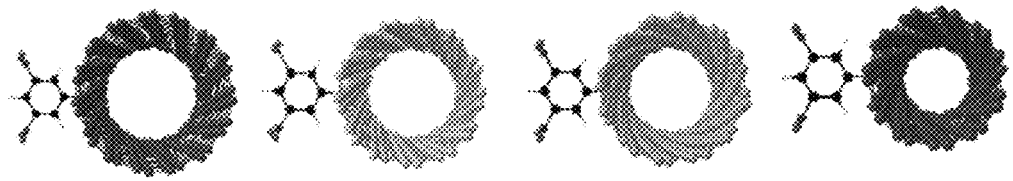
FIG. 10A  FIG. 10B  FIG. 10C  FIG. 10D

ORGANIC COLOR CENTER-TAILORED, SEMICONDUCTING CARBON NANOTUBES AND THEIR METHOD OF MANUFACTURE

CROSS-REFERENCE TO RELATED APPLICATIONS

This application claims the benefit of U.S. provisional application 63/046,969, filed Jul. 1, 2020, and U.S. provisional application 63/217,645, filed Jul. 1, 2021, each of which hereby is incorporated by reference herein in its respective entirety.

STATEMENT REGARDING FEDERALLY SPONSORED RESEARCH OR DEVELOPMENT

This invention was made with government support under PHY1839165 and CHE1904488 awarded by the National Science Foundation. The government has certain rights in the invention.

BACKGROUND

The present disclosure relates generally to carbon nanotubes and other carbon nanomaterials and their method of manufacture. Embodiments of the present disclosure relate to the formation of organic color centers in carbon nanomaterials and related materials. In certain embodiments, the carbon nanotubes are semiconducting, single-wall carbon nanotubes (SWCNTs) tailored to form organic color centers (OCCs).

Organic color centers (OCCs) are sp3 quantum defects intentionally implanted into the sp2 lattice of carbon nanomaterials, particularly carbon nanotubes and more specifically semiconducting single-walled carbon nanotubes (SWCNTs). The implanted sp3 defects create local potential wells in the semiconducting SWCNT host, allowing mobile excitons to be harvested at the trapping defect and converted into infrared photoluminescence (PL) with high efficiency. These properties have motivated the exploration and demonstration of room-temperature quantum light emitters, near-infrared (NIR)-II bioimaging contrast agents, and in situ biological pH sensors. However, many potential applications require large quantities of materials, which require a scalable high-yield method. For example, in the case of bioimaging applications, the in vivo administration to small animals (e.g., mice and rats) typically requires SWCNT concentrations ranging from approximately 0.1 to 10 mg/kg, corresponding to at least milligrams for administration to an adult human. Furthermore, large-scale synthesis is also required to reduce processing costs and minimize batch-to-batch variations.

Previous methods of synthesizing OCC-SWCNTs have involved stabilizing individual SWCNTs using surfactants in an aqueous solution or polymers in an organic solvent. However, the concentration of SWCNTs that are functionalized is low, resulting in the very limited scale. Moreover, using surfactants to stabilize individual SWCNTs incurs a serious tradeoff: strong surfactants, such as sodium deoxycholate (DOC), effectively stabilize SWCNTs by homogeneously and tightly encapsulating the nanotubes, which in turn make the nanotube surface less accessible for subsequent reactions. Alternatively, weaker surfactants, like sodium dodecyl sulfate (SDS), form loose and disordered micelle structures that only partially cover the nanotube sidewalls. The highest concentration of SDS-stabilized SWCNTs is, however, only approximately 18 μg/mL, making it difficult to scale up the chemical reaction.

Furthermore, an OCC typically involves a pair of functional groups bonded to the carbon lattice. While the first functional group can be well-controlled by choosing the specific type of precursors (e.g., aryl functional groups by diazonium salts) as the reactant, the chemical nature of the pairing group remains unclear, with several possibilities proposed, including —H, —OH, or another aryl moiety, and cannot be controlled.

The synthesis of OCC-SWCNTs generally involves implanting $sp^3$ defects onto semiconducting SWCNT surfaces through the formation of C—C covalent bonds. A scalable synthetic route to produce this promising material should thus meet three prerequisites: (1) the ability to process a large amount of SWCNTs as the reactant material; (2) a facile chemistry to create C—C bonds; and (3) a solvent to individually disperse SWCNTs at high concentrations so that the nanotube surfaces are accessible for the OCC-implanting chemistry. The mass production of SWCNTs has been commercially achieved (e.g., up to 10 tons per year scale at OCSiAl), which provides a sufficient source of raw SWCNTs. However, as-synthesized SWCNTs are bundled due to strong van der Waals attractions, making the nanotube surface largely inaccessible to reactant molecules. As a result, individualized SWCNTs are necessary to increase the efficiency of OCC-implanting chemistry.

Compared with existing OCC chemistries, the presently disclosed method of manufacture features significant advantages. For example, one advantage is that in certain embodiments of the present method, the reaction occurs efficiently even at ultrahigh concentrations (for example, greater than 4000 μg/mL), making it readily scalable to synthesize large quantities of OCC-SWCNTs. Another advantage is that certain embodiments of the present method require no surfactants or polymers to disperse the SWCNTs; thus, the nanotube surfaces are "bare," free from molecular coating, and completely accessible for OCC implantation. In certain embodiments, the reaction completes in seconds (versus days for traditional aqueous diazonium salt reactions). Yet another advantage of the present method is that because surfactant dispersion is not required and therefore not limited to the use of a single surfactant, certain embodiments of the present method produce neat OCC-SWCNTs that can be directly encapsulated by specialized molecules/polymers that may be required for subsequent applications, such as chiral purification of OCC-SWCNTs. Also importantly, the present method allows us to control the $2^{nd}$ group of the OCC, leading to the synthetic creation of many new OCC types that have never been possible until this invention. The present method is suitable for facile, efficient, and scalable production of OCC-SWCNTs synthetically accessible for abroad range of applications, such as in imaging, sensing, and quantum information processing.

SUMMARY

The present disclosure provides examples of a method for generating organic color centers in carbon nanomaterials and related materials to provide organic color-center-tailored (derivatized) materials. For example, such a method may comprise mixing the carbon nanomaterial or related material in acid, preferably superacid, with nitrite and an aniline derivative and thereafter adding the mixture to a reactive solvent to form the organic color centers by reaction with the aniline derivative. The method does not require the addition of a radical initiator. In particular, the method does not require the addition of azobisisobutyronitrile (AIBN) or inorganic or organic peroxides, such as di-tert-butyl peroxide. In embodiments, the method does not require heating of the mixture above 50° C. In embodiments, the mixing step can be conducted at room temperature or less than room temperature. In embodiments, the mixing step can be conducted at a temperature between 10° C. and room temperature.

In embodiments, the carbon nanomaterials or other material(s) are dissolved in the acid, particularly the superacid. In specific embodiments, the acid is chlorosulfonic acid, oleum, triflic acid, or 100% sulfuric acid.

In embodiments, the OCC-tailored carbon nanomaterials are collected from the reaction solvent by filtration and dried.

In embodiments, the carbon nanomaterials are carbon nanotubes. In embodiments, the carbon nanomaterials are single-walled or double-walled carbon nanotubes. In embodiments, the carbon nanomaterials are single-walled, double-walled, or multi-walled carbon nanotubes. In embodiments, the carbon nanomaterials are single-walled carbon nanotubes (SWCNTs).

In embodiments, the reactive solvent comprises one or more of water, C1-C6 alkyl alcohols (straight-chain or branched), ammonia, C1-C6 monoalkyamines, C1-C6 dialkylamines, optionally substituted phenol or isotopic variants thereof. In embodiments, the reactive solvent comprises one or more of $H_2O$, $D_2O$, methanol, ethanol, 1-propanol, 1-butanol, 1-pentanol, 1-hexanol, ammonia, methylamine, ethylamine, dimethylamine, diethylamine, phenol, or mixtures thereof. In embodiments, the reactive solvent is a miscible mixture of water with one or more C1-C6 alkyl alcohols. In embodiments, the reactive solvent is an aqueous solution containing one or more of methanol, ethanol, 1-propanol, 1-butanol, 1-pentanol, 1-hexanol, ammonia, methylamine, ethylamine, dimethylamine, diethylamine, or phenol. In embodiments, the reactive solvent is $H_2O$ or an isotopic variant thereof.

In an embodiment, a method is provided for making organic color center (OCC)-tailored carbon nanomaterials where the method comprises the steps of: mixing the carbon nanomaterials with an acid, a nitrite salt, and one or more aniline derivatives; and adding the mixture to a reactive solvent to form the OCC-tailored carbon nanomaterials. In an embodiment, adding the mixture to the reactive solvent precipitates the OCC-tailored carbon nanomaterials. In an embodiment, adding the mixture to the reactive solvent forms and precipitates the OCC-tailored carbon nanomaterials.

In embodiments, the aniline derivative is unsubstituted aniline, or any mono-, di-, tri-, tetra-, or penta-substituted derivative of aniline. In embodiments, aniline derivatives include aminobenzoic acid and any mono-, di-, tri-, or tetra-substituted derivatives of aminobenzoic acid. In specific embodiments, the aniline derivative is 2-fluoro-4-nitroaniline, 4-amino-2-fluorobenzoic acid, or 4-amino-2,3,5,6-tetrafluorobenzoic acid.

In embodiments, the concentration of carbon nanomaterials mixed in the acid is in the range of 1 μg/mL to 50,000 μg/mL. In embodiments, the concentration of carbon nanomaterials mixed in the acid is in the range of 20 μg/mL to 5,000 μg/mL. In embodiments, the concentration of carbon nanomaterials mixed in the acid is in the range of 20 μg/mL to 500 μg/mL. In embodiments, the concentration of carbon nanomaterials mixed in the acid is in the range of 50 μg/mL to 500 μg/mL. In embodiments, the concentration of carbon nanomaterials mixed in the acid is in the range of 50 μg/mL to 1,000 μg/mL. In embodiments, the concentration of carbon nanomaterials mixed in the acid is in the range of 20 μg/mL to 250 μg/mL. In embodiments, the concentration of carbon nanomaterials dissolved in the acid is in the range from 1 μg/mL to 50,000 μg/mL. In embodiments, the concentration of carbon nanomaterials dissolved in the acid is in the range of 20 μg/mL to 5,000 μg/mL. In embodiments, the concentration of carbon nanomaterials dissolved in the acid is in the range of 20 μg/mL to 500 μg/mL. In embodiments, the concentration of carbon nanomaterials dissolved in the acid is in the range of 50 μg/mL to 500 μg/mL. In embodiments, the concentration of carbon nanomaterials dissolved in the acid is in the range of 50 μg/mL to 1,000 μg/mL. In embodiments, the concentration of carbon nanomaterials dissolved in the acid is in the range of 20 μg/mL to 250 μg/mL.

In general, any source of nitrite can be used in the example methods of the present disclosure. More specifically, a nitrite salt is employed. In an embodiment, the nitrite salt is selected from the group consisting of $LiNO_2$, $NaNO_2$, $KNO_2$, $RbNO_2$, $CsNO_2$, $Mg(NO_2)_2$, $Ca(NO_2)_2$, $Sr(NO_2)_2$, $Ba(NO_2)_2$, $Al(NO_2)_3$ and any mixtures thereof.

In embodiments, the aniline derivative to carbon molar ratio ([aniline]:[C]) ranges from 0.1:50 to 10:50. In embodiments, the aniline derivative to carbon molar ratio rages from 0.5:50 to 2:50. In embodiments, the aniline derivative to carbon molar ratio rages from 0.9:50 to 1.1:50.

In embodiments, the molar ratio of aniline derivative to nitrite ranges from 0.5 to 2. In an embodiment, the molar ratio of aniline derivative to nitrite ranges from 0.9 to 1.1

The present disclosure also provides organic color center (OCC)-tailored carbon nanotube prepared by the method as described herein. In embodiments, the (OCC)-tailored carbon nanomaterials are (OCC)-tailored carbon nanotubes. In embodiments, the (OCC)-tailored carbon nanotubes are (OCC)-tailored SWCNTs. In specific embodiments, the OCC-tailored SWCNTs are those prepared by reaction as described herein wherein the aniline derivative is a compound of formula I as described herein. In specific embodiments, the OCC-tailored SWCNTs are those prepared by reaction as described herein wherein the aniline derivative is 2-fluoro-4-nitroaniline, 4-amino-2-fluorobenzoic acid, or 4-amino-2,3,5,6-tetrafluorobenzoic acid.

In embodiments, the carbon nanotube products of the method herein are suitable for producing chirality pure materials.

In embodiments, the carbon nanotube products of the method herein are shorter than 50 nanometers. In embodiments, the carbon nanotube products of the method are longer than 3 micrometers. In embodiments, the carbon nanotube products of the method range from 50 nanometers to 3 micrometers in length.

In embodiments, the carbon nanotube products of the method have a diameter ranging from 0.4 to 2.0 nm. In embodiments, the carbon nanotube products of the method have a diameter ranging from 0.5 to 1.3 nm. In embodiments, the carbon nanotube products of the method have a diameter ranging from 0.9 to 1.3 nm. In embodiments, the carbon nanotube products of the method have a diameter of 1 or greater. In embodiments, the carbon nanotube products of the method have a diameter ranging from 1.0 to 1.3 nm.

In embodiments, the (OCC)-tailored products of the method are in a form of neat material that can be directly individualized by any known method, e.g., by polymers or DNAs, to form a nanocomposite. In embodiments, the (OCC)-tailored carbon nanotube products of the method are in a form of neat material that can be directly individualized by any known method, e.g., by polymers or DNAs, to form a nanocomposite. In embodiments, the (OCC)-tailored SWCNTs of the method are in a form of neat material that can be directly individualized by any known method, e.g., by polymers or DNAs, to form a nanocomposite.

In embodiments, the products of the method are suitable for use as field-effect transistors. In embodiments, the products of the method are suitable for use as light-emitting diodes. In embodiments, the products of the method are suitable for use as near-infrared emitters. In embodiments, the products of the method are suitable for use as quantum light sources. In embodiments, the products of the method are suitable for use as biochemical sensors. In embodiments, the products of the method are suitable for use as drug delivery agents.

Other aspects and embodiments will be apparent based on a review of the non-limiting detailed description, drawings and examples disclosed herein.

BRIEF DESCRIPTION OF THE DRAWINGS

FIG. 1A shows that the reaction occurs by mixing SWCNTs, aniline derivatives, where R is ring substitution in addition to $NH_2$ and nitrite salt (e.g., $NaNO_2$) in acid (i.e., superacid, e.g., chlorosulfonic acid), followed by introducing the mixture into water. Black solid is collected by filtration and vacuumed dried. The resulting OCC-SWCNTs are schematically illustrated. FIG. 1B is a graph of Raman scattering from thin films of $C_6H_3(NO_2)_2$—OCC-tailored-SWCNTs (grey) and pristine SWCNTs (black) showing the Raman D and G peaks, and FIG. 1C illustrates the spatial maps of the Raman D/G ratios (plotted in grey-tone scale). The laser excitation is 633 nm.

FIG. 2A shows the PL excitation-emission map of $C_6H_3(NO_2)_2$—OCC-tailored-SWCNTs in 2 wt/v % DOC-$D_2O$ solution. FIG. 2B shows single-particle PL imaging of $C_6H_3(NO_2)_2$—OCC-tailored-SWCNTs. FIG. 2C shows the hyperspectral PL image of an individual $C_6H_3(NO_2)_2$—OCC-tailored-(6,5)-SWCNT from FIG. 2B.

FIG. 3A shows the PL spectra (at 565 nm excitation) of pristine SWCNTs (black) and $C_6H_3(NO_2)_2$—OCC-tailored-SWCNT (grey) dispersed in 2 wt/v % DOC-$D_2O$ solution. FIG. 3B is a graph of the PL intensity ratio of E11−/E11 as a function of the initial relative concentration of the aniline derivative and carbon. By adjusting the initial relative amounts of the reagents, the PL intensity of the synthesized OCC-SWCNTs can be controlled. The $C_6H_3(NO_2)_2$—OCC-tailored-SWCNT of the PL spectra of FIG. 3A was prepared using the molar ratio of [aniline]/[C]($10^{-2}$) of 2, the maximum value in FIG. 3B.

FIG. 4A shows the PL spectrum of 4-nitro-aniline OCC-SWCNT. FIG. 4B shows the PL spectrum of 2-fluoro-4-nitro aniline OCC-SWCNT. FIG. 4C shows the PL spectrum of 4-hydroxy-aniline OCC-SWCNT. FIG. 4D shows the PL spectrum of 4-aminobenzoic acid OCC-SWCNT. FIG. 4E shows the PL spectrum of 4-amino-2-fluorobenzoic acid OCC-SWCNT. FIG. 4F shows the PL spectrum of 4-amino-3-fluorobenzoic acid OCC-SWCNT. FIG. 4G shows the PL spectrum of 4-amino-2,3,5,6-tetrafluorobenzoic acid OCC-SWCNT. FIG. 4H shows the PL spectrum of 4-chloroaniline OCC-SWCNT. FIG. 4I shows the PL spectrum of 2-iodoaniline OCC-SWCNT. The 2-fluoro-4-nitro-aryl, 4-amino-2-fluorobenzoic acid, and 4-amino-2,3,5,6-tetrafluorobenzoic acid OCCs are synthetically achieved for the first time, enabled by this one-pot reaction.

FIG. 5A shows the PL spectrum (at 565 nm excitation) and FIG. 5B shows the excitation-emission map of the $C_6H_3(NO_2)_2$—OCC-tailored-SWCNT sample that was directly stabilized by the S2E process.

FIG. 6A shows the Atomic Force Microscope (AFM) imaging and FIG. 6B is a graph of length distribution of the $C_6H_3(NO_2)_2$—OCC-tailored-SWCNT sample produced from the separate S2E step.

FIG. 7A shows the PL spectrum (at 565 nm excitation) and FIG. 7B shows the excitation-emission map of the $C_6H_3(NO_2)_2$—OCC-tailored-SWCNT sample produced from the separate S2E step.

FIGS. 10A-10F. Single chirality-enriched OCC-SWCNTs. DOC-$D_2O$ solutions of (8,7)-(FIG. 10A), (7,6)-(FIG. 10B), (7,5)-(FIG. 10C), and (6,5)-enriched (FIG. 10D) $C_6H_3(NO_2)_2$—OCC-tailored-SWCNTs, along with their corresponding PL excitation-emission maps. Due to the strong water absorption above the wavelength of 1350 nm, the defect PL ($E_{11}^-$) peak could not be directly detected in the aqueous solutions of $C_6H_3(NO_2)_2$—OCC-tailored-(12,1)-SWCNT and $C_6H_3(NO_2)_2$—OCC-tailored-(8,7)-SWCNT. The red (1) and green (2) stars in the PL excitation-emission map of FIG. 10A are the peak positions measured by the hyperspectral imaging of individual nanotubes deposited on a substrate. FIG. 10E shows the PL spectra of $C_6H_3(NO_2)_2$—OCC-tailored-SWCNT made from different chiralities. The spectra were fitted with Voigt functions. The arrows indicate the $E_{11}$ wavelength of $C_6H_3(NO_2)_2$—OCC-tailored-SWCNT. FIG. 10F is a graph of the correlation of $E_{11}^-$ (Wavelength (nm) on left axis (black), Energy (eV) on right axis (grey) with the host nanotube diameters for $C_6H_3(NO_2)_2$—OCC-tailored-SWCNT.

DETAILED DESCRIPTION

Figure 1A:
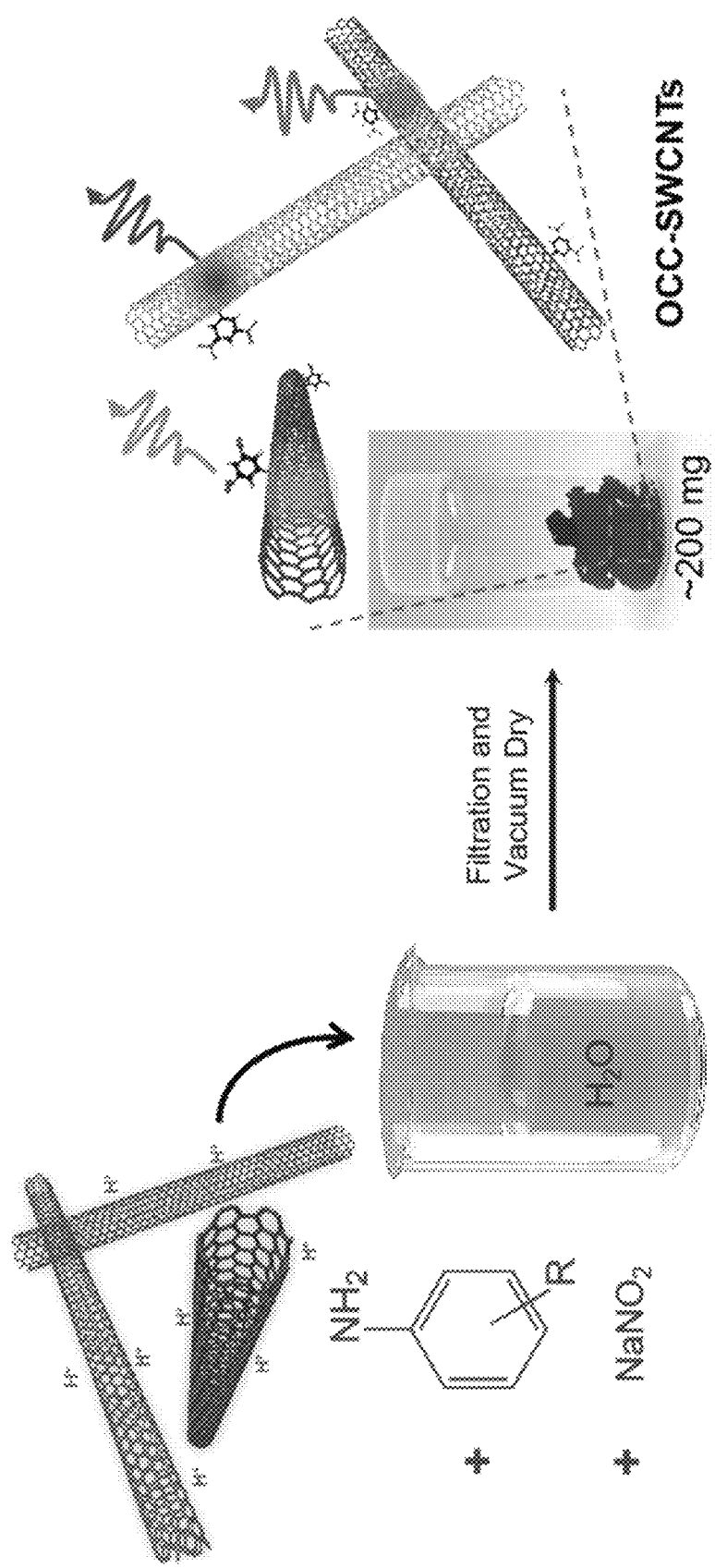
FIGS. 1A-1C. Illustrate schematically an exemplary one-pot, large-scale synthesis of OCC-SWCNTs.

Organic color center-tailored semiconducting single-walled carbon nanotubes are a rising family of synthetic quantum emitters that display bright defect photoluminescence uniquely tunable for imaging, sensing, and quantum information processing. Embodiments of a high-yield synthetic route that is capable of producing these materials well exceeding the current μg/mL scale. Adding an acid solution of raw carbon nanotubes, a nitrite salt, and an aniline derivative into a reactive solvent, such as water and ethanol, readily leads to the synthesis of organic color center-tailored nanotubes. This simple one-pot reaction is highly scalable (yielding hundreds of milligrams of materials in a single run), efficient (reaction completes in seconds), and versatile (making the synthesis of several new organic color centers that are otherwise impossible). The implanted organic color centers can be easily tailored by choosing from a wide range of aniline derivatives and solvents that are either commercially available or which can be readily prepared by art-recognized methods. Useful aniline derivatives include many fluoroaniline and aminobenzoic acid derivatives, that are difficult to convert into diazonium salts. The chemistry works for all the nanotube chiralities investigated. The synthesized materials are neat solids that can be readily dispersed in either water or an organic solvent by a surfactant or polymer depending on the specific application. The nanotube products can also be further sorted into single chirality-enriched fractions with defect-specific photoluminescence that is tunable over approximately 1100 to approximately 1550 nm. This chemistry thus paves a way to the large-scale synthesis of organic color centers for many potential applications that require large quantities of materials.

In a specific embodiment, large-scale synthesis of organic color center-tailored SWCNTs can be achieved by simply mixing SWCNTs, a nitrite salt, such as NaNO$_2$, and an aniline derivative in superacid, such as chlorosulfonic acid, then introducing the mixture into water or another reactive solvent such as ethanol. In embodiments, no radical initiator is added to the mixture. In embodiments, the synthesis is conducted at temperatures of 50° C. or less. In embodiments, the synthesis is conducted at room temperature.

Compared with existing OCC chemistries, this one-pot reaction features significant advantages, including: (1) the reaction occurs efficiently even at ultrahigh concentrations (>4000 μg/mL), making it readily scalable to synthesize large quantities of OCC-tailored carbon nanomaterials; (2) no surfactants or polymers are required to disperse the carbon nanomaterials (e.g., SWCNTs), thus the nanotube surfaces are "bare", free from molecular coating, and completely accessible for OCC implantation; (3) the reaction completes in seconds (versus days for aqueous diazonium salt reactions); and (4) distinct from existing methods that require surfactant dispersion and work only for certain surfactants, this method produces neat OCC-carbon nanomaterials (e.g., OCC-SWCNTs) that can be directly encapsulated by specialized molecules/polymers that are required for subsequent applications (e.g., chiral purification of OCC-SWCNTs). This facile, efficient, and scalable method allows large quantities of OCC-carbon nanomaterials, particularly OCC-SWCNTs, synthetically accessible for a broad range of applications in imaging, sensing, and quantum information processing.

Aniline Derivatives

Aniline and any substituted aniline can be employed as a reagent in the methods herein. Aniline derivatives include aminobenzoic acid and substituted aminobenzoic acid. Aniline derivatives include aniline substituted with any functional group that is non-reactive under the reaction conditions described herein. Appropriate functional groups include those that are stable to acidic conditions as described herein. Aniline derivatives useful herein include those substituted with one or two amino groups in addition to the amino group of the aniline. Aniline derivatives include salts of aniline, such as aniline hydrochloride. Aniline derivatives include salts of aminobenzoic acid.

In embodiments, the aniline derivative is a compound of formula:

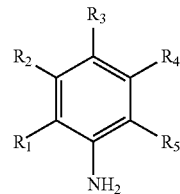

or a salt thereof, where:
$R_1$-$R_5$ are independently selected from the group(s) consisting of hydrogen, halogen, amino, hydroxyl, alkyl, alkenyl, alkynyl, alkoxy, aryl, aryloxy, arylalkyl, arylalkoxy, haloalkyl, haloalkoxy, —COOH, —COOR, —NO$_2$, —SO$_3$H, —C(R)=N—OH, —C(NH$_2$)=N—OH, —CO—NH$_2$, —CS—NH$_2$, —CN, —NC, —OCN, —NCO, —SCN, —NCS, —SH, —SR, —COH, —COR, —CO—N(R)$_2$, —NH(R), and —N(R)$_2$, where alkyl, alkenyl, alkynyl, alkoxy, aryl, aryloxy, arylalkyl, and arylalkoxy, are optionally substituted, and where each R is independently an optionally substituted alkyl group, or an optionally substituted aryl group.

Optional substitution of aniline functional groups includes substitution with one or more halogen, amino, hydroxyl, C1-C3 alkyl, C1-C3 alkoxy, phenyl, benzyl, phenoxy, benzoxy, —CF$_3$, —OCF$_3$, —COOH, —COOR', —NO$_2$, —SO$_3$H, —C(R')=N—OH, —C(NH$_2$)=N—OH, —CO—NH$_2$, —CS—NH$_2$, —CN, —NC, —OCN, —NCO, —SCN, —NCS, —SH, —SR', —COH, —COR', —CO—N(R')$_2$, —NH(R'), or —N(R')$_2$, where each R' is an unsubstituted alkyl and particularly is an unsubstituted C1-C3 alkyl group. In more specific embodiments, optional substitution is substitution with one or more halogen, amino, hydroxyl, C1-C3 alkyl, C1-C3 alkoxy, —CF$_3$, —OCF$_3$, —COOH, —NO$_2$, —SO$_3$H, —C(R')=N—OH, —C(NH$_2$)=N—OH, —CO—NH$_2$, —CS—NH$_2$, —COH, —COR', —CO—N(R')$_2$, —NH(R'), or —N(R')$_2$. In additional specific embodiments, optional substitution is substitution with one or more halogen, amino, hydroxyl, C1-C3 alkyl, C1-C3 alkoxy, —CF$_3$, —OCF$_3$, —COOH, —NO$_2$, or —SO$_3$H. In specific embodiments herein, the aniline derivatives do not carry any —SO$_3$H groups.

In embodiments, the aniline derivative is selected from the group consisting of: 3,5-dinitroaniline, 4-nitroaniline, 4-aminobenzoic acid, 2-fluoro-4-nitroaniline, 4-amino-2-fluorobenzoic acid, 4-amino-3-fluorobenzoic acid, 4-amino-2,3,5,6-tetrafluorobenzoic acid, 2-iodoaniline, 4-chloroaniline, 4-aminophenol, 2-aminobenzamidoxime, 3-aminobenzamidoxime, 4-aminobenzamidoxime, 2-amino-5-chlorobenzyl alcohol, 4-amino-2,3-difluorophenol, 4-amino-3,5-difluorophenol, 2-amino-5-fluorophenol, 3-aminothiobenzamide, 2-chloro-4,5-difluoroaniline, 3-chloro-2-fluoroaniline, 6-chloro-2-fluoro-3-methoxyaniline, 3-chloro-4-methylaniline hydrochloride, 3-chloro-4-nitroaniline, 3-chloro-5-(trifluoromethoxy)aniline, 2,5-diaminobenzenesulfonic acid, 2,3-dichloro-6-(trifluoromethyl)aniline, 2,6-dichloro-3-(trifluoromethyl)aniline, 4,5-difluoro-2-methoxyaniline, 3,5-difluoro-2-methoxyaniline, 4-fluoro-2,3-dimethylaniline, 4-fluoro-3,5-dimethylaniline, 2-fluoro-4-methoxyaniline, 3-fluoro-2-methoxyaniline, 5-fluoro-2-methoxyaniline, 2-fluoro-5-(trifluoromethoxy)-aniline, 2-iodo-4,6-dimethylaniline, 4-methoxy-3,5-dimethylaniline, 3-methyl-5-(trifluoromethoxy)aniline, aniline-2-sulfonic, 3-aminobenzenesulfonic acid, 4-aminotoluene-3-sulfonic acid, and phenylenediamine.

In more specific embodiments, the aniline derivative is 2-fluoro-4-nitroaniline, 4-amino-2-fluorobenzoic acid, or 4-amino-2,3,5,6-tetrafluorobenzoic acid.

In specific embodiments, the aniline derivative is substituted with one or two monovalent substituents as described herein. In specific embodiments, the aniline derivative is substituted with two or three monovalent substituents as described herein. In specific embodiments, the aniline derivative is substituted with three or four monovalent substituents as described herein.

Substituents for the derivatization of aniline are typically monovalent functional groups. Monovalent functional groups include, among others, alkyl, alkenyl, alkynyl, alkoxy, aryl, aryloxy, arylalkyl, arylalkoxy, haloalkyl, or haloalkoxy. Other monofunctional substituents are illustrated herein by their formulas, which are well known in the art.

Alkyl groups include straight-chain or branched alkyl groups. Alkyl groups can generally include 1-20 carbon atoms, or 1-10 carbon atoms, or more specifically 1-6 carbon atoms (C1-C6 alkyl) or yet more specifically 1-3 carbon atoms (C1-C3 alkyl). Alkyl groups also include cycloalkyl groups which contain one or more a 3-12-member carbon ring, or a 3-10-member carbon ring, or more specifically a 3-6 carbon ring. Cycloalkyl groups include among others, bicyclic groups. Alkyl and cycloalkyl groups are generally optionally substituted.

Alkenyl groups are monovalent hydrocarbon groups containing one or more double bond(s), and more typically one double bond. Alkenyl groups can generally include 1-20 carbon atoms, or 2-10 carbon atoms, or more specifically 2-6 carbon atoms (C1-C6 alkenyl) or yet more specifically 2-3 carbon atoms (C1-C3 alkenyl). Alkenyl groups also include cycloalkenyl groups which contain one or more 3-12-member carbon ring, or a 3-10-member carbon ring, or more specifically a 5- or 6-carbon ring having one or more double bonds. Cycloalkenyl groups include among others, bicyclic groups. Alkenyl and cycloalkenyl groups are generally optionally substituted.

Alkynyl groups are monovalent hydrocarbon groups containing one or more triple bond(s) and more typically one triple bond. Alkynyl groups can generally include 1-20 carbon atoms, or 2-10 carbon atoms, or more specifically 2-6 carbon atoms (C1-C6 alkynyl) or yet more specifically 2-3 carbon atoms (C1-C3 alkynyl). Alkenyl groups also include cycloalkynyl groups which contain a 5-12-member carbon ring, or a 5-10-member carbon ring, or more specifically a 5- or 6-carbon ring having one or more triple bonds. Alkenyl and cycloalkenyl groups are generally optionally substituted.

Aryl groups contain one or more aromatic rings, and more particularly one or two aromatic rings, such as a phenyl ring, a naphthyl ring, or a biphenyl ring. Aryl groups may contain fused aromatic rings or aromatic rings bonded through a C—C bond. Aryl groups are generally optionally substituted. Aryl groups include among others optionally substituted phenyl groups.

Arylalkyl groups are monovalent alkyl radicals as defined above substituted with an aryl group as defined above. An exemplary arylalkyl group is a benzyl group. Arylalkyl groups are generally optionally substituted.

An alkoxy group is a —O-alkyl group, where alkyl is as defined above. An aryloxy group is a —O-Aryl group, where aryl is as defined above. An arylalkoxy is a —O-arylalkyl group, where an arylalkyl group is as defined above.

Haloalkyl groups are alkyl groups that are optionally substituted with one or more halogens. Haloalkyl groups include those having 1-6 carbon atoms (C1-C6-haloalkyl) or more specifically 1-3 carbon atoms (C1-C3-haloalkyl). Halogens include F, Cl, Br, and I and a given haloalkyl group may be substituted with one or more halogens that are the same or different. Exemplary haloalkyl groups include among others —$CF_3$, —$CF_2CF_3$, —$CH_2CF_3$, —$CH_2Cl$, —$CHFCHCl_2$. Haloalkoxy groups are —O-haloalkyl groups, where haloalkyl groups are as defined herein.

Acids

In general, any acid in which the carbon nanomaterial is at least in part soluble can be employed in the methods herein. Preferably, the acid is a superacid or 100% sulfuric acid. Preferably, the carbon nanomaterials are soluble in the selected acid or superacid to achieve a concentration of 1 µg/mL or higher in the acid. More preferably the carbon nanomaterials are soluble in the selected acid or superacid to achieve a concentration of 20 µg/mL or higher in the acid. Yet more preferably the carbon nanomaterials are soluble in the selected acid or superacid to achieve a concentration of 100 µg/mL or higher in the acid. Chlorosulfuric acid is a more preferred acid.

Bronsted superacids, Lewis superacids, and conjugate Bronsted-Lewis superacids can be employed in the method herein. Bronsted superacids include, for example, perchloric acid, chlorosulfonic acid, fluorosulfonic acid, trifluoromethanesulfonic acid (triflic acid), and higher perfluoroalkane sulfonic acids (e.g., pentafluoroethane sulfonic acid, nonafluorobutane sulfonic acid, undecafluoropentane sulfonic acid, tridecafluorohexane sulfonic acid, heptadecafluorooctane sulfonic acid). Lewis superacids include, for example, antimony pentafluoride and arsenic pentafluoride. Bronsted-Lewis superacids include, for example, oleums (fuming sulfuric acid, i.e., sulfuric acids containing sulfur trioxide, e.g., up to 20% or up to 30% sulfurtrioxide); magic acid (mixtures of fluorosulfuric acid and antimony pentafluoride, typically in 1:1 molar ratio); polyphosphoric acid oleum mixtures, tetra(hydrogen sulfate) boric acid-sulfuric acid, fluorosulfuric acid-sulfur trioxide mixtures, fluorosulfuric acid-arsenic pentafluoride mixtures, fluorosulfonic acid-hydrogen fluoride-antimony pentafluoride mixtures, fluorosulfonic acid-antimony pentafluoride-sulfur trioxide mixtures, fluoroantimonic acid, and tetrafluoroboric acid. While not formally a superacid, 100% sulfuric acid can be employed in the methods herein.

Reactive Solvent

In the methods herein, an acidic mixture of carbon nanotubes with nitrite is added to a reactive solvent. In embodiments, the reactive solvent participates in the reaction. Reactive solvents include, among others, water, alkyl alcohols (particularly C1-C6 alkyl alcohols), optionally-substituted phenols, ammonia, monoalkyl amines, and dialkyl amines (particularly alkyl amines wherein the alkyl group is a C1-C6 alkyl group or a C1-C3 alkyl group) as well as mixtures of these solvents. In each case, isotopic variants of a solvent may be employed in whole or in part. For example, the reactive solvent may be $H_2O$, $D_2O$, or any mixture thereof. In embodiments, the reactive solvent is or can contain $H_2O$, $D_2O$, methanol, ethanol), propanol (including any isomer thereof), butanol (including any isomer thereof), pentanol (including any isomer thereof), hexanol (including any isomer thereof), ammonia, methylamine, ethylamine, dimethylamine, diethylamine, phenol or mixtures of any of the foregoing. Useful substituted phenols include those substituted with one or more C1-C3 alkyl groups, and/or one or more halogens. Preferred alcohol solvents or co-solvents include methanol, ethanol, 1-propanol, 1-butanol, 1-pentanol, and 1-hexanol. The reactive solvent can also be an aqueous solution containing any one of the above-listed solvents. Aqueous solvents include among others aqueous alcohols, aqueous ammonia, or aqueous amines.

Water and other reactive solvents used in reactive solvents and particularly in aqueous dispersions herein is of appropriate quality for the intended application of products as will be appreciated and understood by one skilled in the art. In many applications, highly purified water, such as nanopure water, where the term nanopure is used herein as it is generally used in the art of nanomaterials and particularly in the field of carbon nanomaterials. In embodiments, high purity deionized water may be employed. For certain applications or methods of analysis, it may be appropriate to employ deuterated water or tritiated water, or isotopic variants of other reactive solvents. One skilled in the art can select the appropriate purity of water or other solvent or isotopic variants thereof for the methods herein, In specific embodiments, the reactive solvent is a nucleophilic solvent or mixture thereof. In more specific embodiments, the nucleophilic solvent is a nucleophilic solvent is or can include methanol, ethanol, n-propanol, and liquid ammonia.

Carbon Nanomaterials and Other Materials

The OCC-tailoring method herein is exemplified with carbon nanotubes and more specifically with SWCNTs, and yet more specifically with semiconducting SWCNTs. The method herein can be extended to other carbon nanomaterials including among others graphite, graphite oxide, graphene, graphene nanoribbons, graphene quantum dots. The methods herein can also be extended to boron nitrite, and boron nitrite nanotubes.

As to any of the above compounds or functional groups which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

In embodiments herein, the acidic mixture containing carbon nanomaterial, nitrite, and aniline derivatives does not contain any radical initiator. In embodiments, mixing of the components is performed at a temperature less than 80° C. In embodiments, mixing of the components is performed at a temperature equal to or less than 50° C. In embodiments, mixing of the components is performed at a temperature equal to or less than 40° C. In embodiments, mixing at the components is performed at a temperature between 10° C. and room temperature. In embodiments, the reactive solvent is not heated before or after addition of the mixture. In embodiments, the reactive solvent is at room temperature or less before addition of the mixture. In embodiments, the reactive solvent is cooled below room temperature before and/or after addition of the mixture.

In embodiments, the reactive solvent is a solvent other than a halogenated aromatic, such as 1,2-dichlorobenzene. In embodiments, OCC-tailoring is not carried out in a medium containing a halogenated aromatic hydrocarbon, such as 1,2-dichlorobenzene. In embodiments herein, the OCC-tailoring method herein is not electrochemically induced.

In embodiments herein, the carbon nanotube products of the OCC-tailoring method herein are not soluble in water. In embodiments herein, the OCC-tailored SWCNT products of the OCC-tailoring method herein are not soluble in water.

Compounds herein may contain chemical groups (acidic or basic groups) that can be in the form of salts. Exemplary acid addition salts include halides (including chorides, fluorides, bromides and iodides), acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like. More specifically, aniline derivatives herein may be in the form of hydrohalide salts, such as hydrochlorides, hydrofluorides, hydrobromides or hydroiodides.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long-chain halides (e.g., decyl, lauryl, myristyl and stearyl chlorides, bromides and iodides), aralkyl halides (e.g., benzyl and phenethyl bromides), and others.

Salts herein include "pharmaceutically acceptable salts," if appropriate for the selected application of products of the methods herein. "Pharmaceutically acceptable salts" refer to those salts which retain the biological effectiveness and properties of the free bases or free acids, and which are not biologically or otherwise undesirable. Pharmaceutically acceptable salts comprise pharmaceutically-acceptable anions and/or cations.

Compounds described herein, and salts thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention. Additionally, compounds herein may have trans and cis isomers and may contain one or more chiral centers, and therefore exist in enantiomeric and diastereomeric forms. The description includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The compounds herein may be used in the free or hydrate form.

With respect to the various compounds of the invention, the atoms therein may have various isotopic forms, e.g., isotopes of hydrogen include deuterium and tritium. All isotopic variants of compounds of the invention are included within the invention and particularly included at deuterium and 13C isotopic variants. It will be appreciated that such isotopic variants may be useful for carrying out various chemical and biological analyses, investigations of reaction mechanisms and the like. Methods for making isotopic variants are known in the art.

All references throughout this application, for example, patent documents including issued or granted patents or equivalents; patent application publications; and non-patent literature documents or other source material; are hereby incorporated by reference herein in their entireties, as though individually incorporated by reference.

Hudson et al. 2004 J. Amer. Chem. Soc. 126, 11158-11159 relates to covalent functionalization of single-walled nanotubes in fuming sulfuring acid providing SWNT-arylsulfonic acids that are soluble in water. This reference is incorporated by reference herein in its entirety as an indication of the state of the art.

Bahr et al. 2001 Chem. Mater. 13:3823-3824 relates to highly functionalized carbon nanotubes using in situ generated diazonium compounds. This reference is incorporated by reference herein in its entirety as an indication of the state of the art.

US published application US2007028087 relates to methods of functionalizing carbon nanotubes (CNTs) in acidic media. The reference reports dispersion in a substantially unbundled state, and functionalized according to one or more of a variety of functionalization processes. This reference is incorporated by reference herein in its entirety as an indication of the state of the art.

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups, including any isomers and enantiomers of the group members, and classes of compounds that can be formed using the substituents are disclosed separately. When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the disclosure.

Every formulation or combination of components described or exemplified can be used to practice the embodiments of the present disclosure, unless otherwise stated. Specific names of compounds are intended to be exemplary, as it is known that one skilled in the art can name the same compounds differently. When a compound is described herein such that a particular isomer or enantiomer of the compound is not specified, for example, in a formula or in a chemical name, that description is intended to include each isomers and enantiomer of the compound described individual or in any combination.

One skilled in the art will appreciate that methods, device elements, starting materials, and synthetic methods other than those specifically exemplified can be employed in the practice of the embodiments of the present disclosure without resorting to undue experimentation. All art-known functional equivalents, of any such methods, device elements, starting materials, and synthetic methods are intended to be included in the present disclosure and embodiments thereof. Whenever a range is given in the specification, for example, a temperature range, a time range, or a composition range, all intermediate ranges, and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. Embodiments illustratively described herein suitably may be practiced in the absence of any element(s) or limitation(s) not specifically disclosed herein.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

THE EXAMPLES

Example 1

Additional details of the following methods and experiments can be found in Luo, H B, et al. (2019) ACS Nano 13(7):8417-8424 and its Supporting Information available at the American Chemical Society publications web site as DOI: 10.1021/acsnano.9604087. This reference and its Supporting Information are each incorporated by reference herein in its entirety.

This example describes a one-pot method for achieving large-scale synthesis of organic color center materials as exemplified for the preparation of OCC-SWCNTs at high concentrations (>4000 μg/mL) by an efficient reaction process that completes in seconds. This exemplary one-pot reaction involves simply mixing raw SWCNTs, an aniline derivative, and $NaNO_2$ in chlorosulfonic acid, and then adding the mixture into nanopure water. The resultant OCC-SWCNTs can be directly sorted into single-chirality enriched OCC-SWCNTs featuring characteristic defect PL.

Figure 1B:
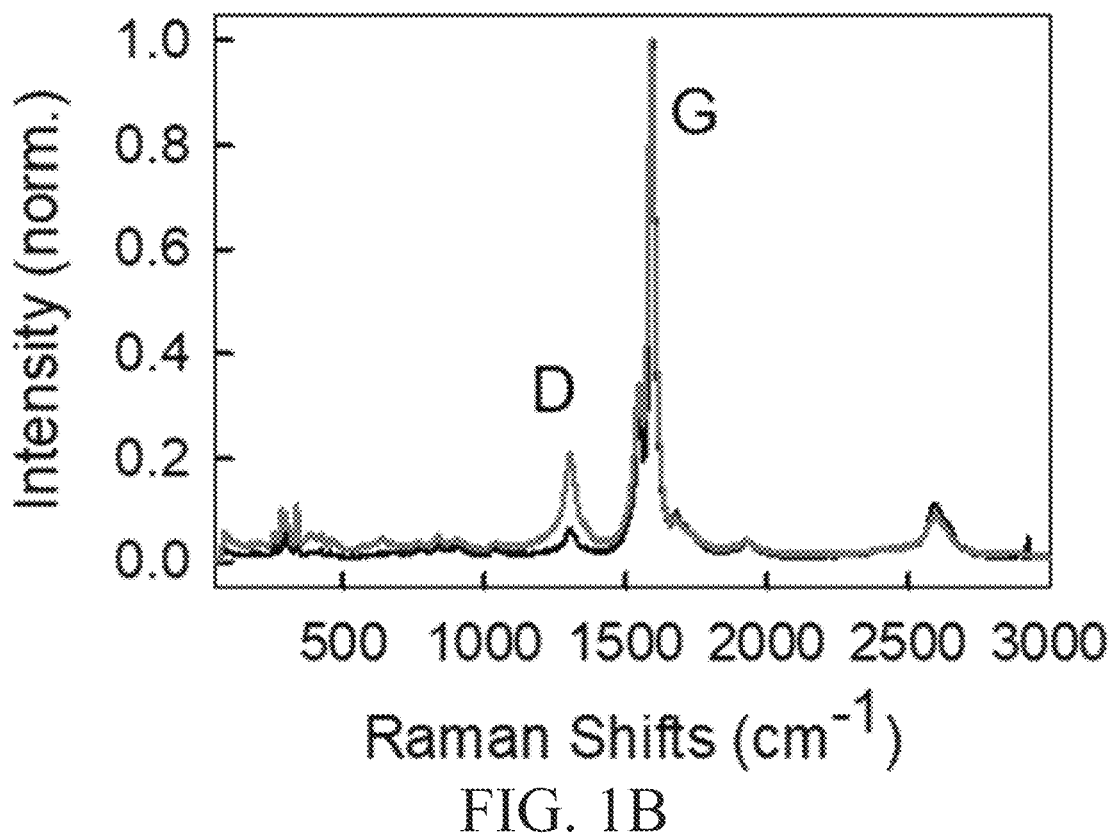
Figure 1C:
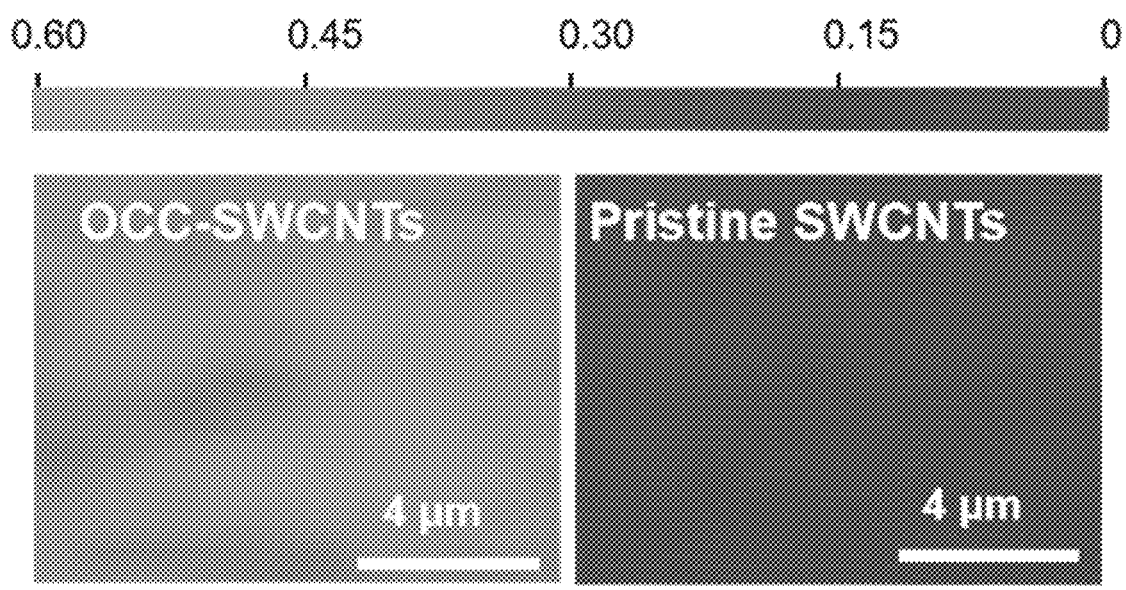

FIG. 1A schematically describes this one-pot synthesis of OCC-SWCNTs. As a demonstration of this technique, raw nanotube powders (CoMoCAT SG 65i), $NaNO_2$, and 3,5-dinitroaniline were mixed in chlorosulfonic acid, and then slowly added into nanopure water. This resulted in the synthesis OCC-SWCNTs, mainly 3,5-dinitroaryl-OCC tailored-(6,5)-SWCNTs (hereafter referred as $C_6H_3(NO_2)_2$—OCC-tailored-(6,5)-SWCNT), as black precipitates, which can be collected via vacuum filtration. The reaction resulted in a covalent modification to the $sp^2$ carbon lattice which was confirmed by Raman spectroscopy, which revealed a significant increase of the D/G ratio (the intensity of the D peak at approximately 1300 $cm^{-1}$ to the G peak at approximately 1600 $cm^{-1}$) to approximately 0.5, compared with approximately 0.1 for the starting raw SWCNTs (FIGS. 1B and 1C). The one-pot reaction allowed the synthesis of OCC-SWCNTs at the hundreds of milligrams scale in a straightforward manner. FIG. 1A shows a batch of $C_6H_3(NO_2)_2$—OCC-tailored-SWCNT weighing approximately 200 mg.

Figure 2A:
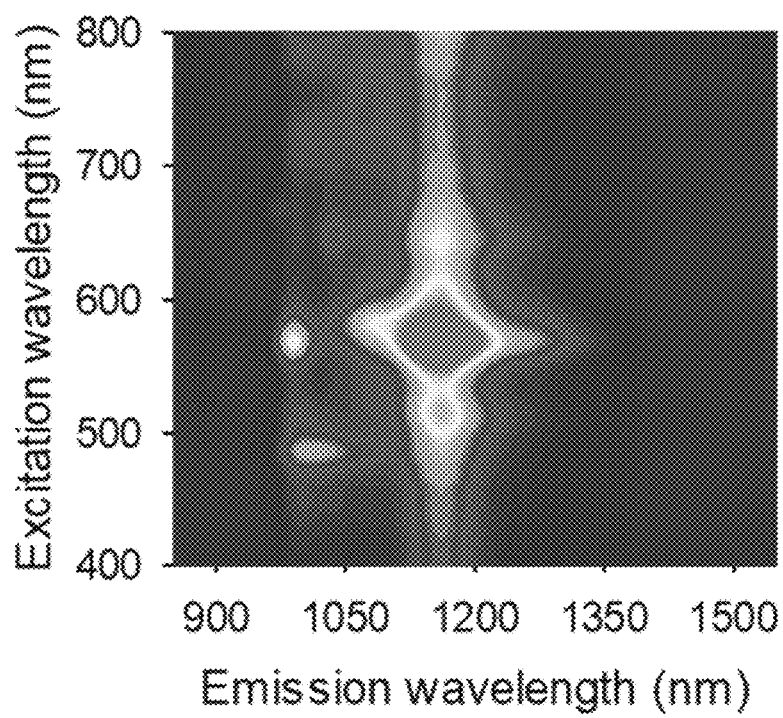
FIGS. 2A-2C. $C_6H_3(NO_2)_2$—OCC-tailored-SWCNTs fluoresce brightly in the shortwave infrared.
Figure 3A:
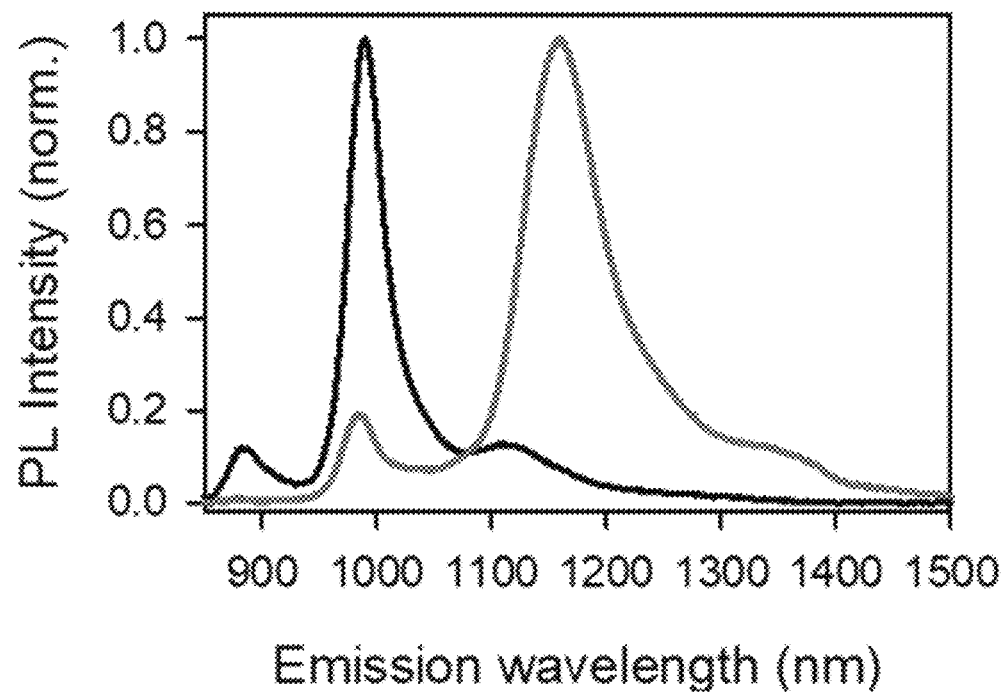
FIGS. 3A-3B.

To characterize the photoluminescence properties, the synthesized $C_6H_3(NO_2)_2$—OCC-tailored-SWCNT material was dispersed in 2 wt/v % $DOC-D_2O$ and the excitation-emission map was measured (FIG. 2A). A bright defect PL ($E_{11}^-$) was observed at approximately 1160 nm, which is red-shifted by 170 nm (184 meV) from the native En emission of pristine (6,5)-SWCNTs (FIG. 3A). This $E_{11}^-$ PL originates from the mobile excitons that are efficiently trapped at the OCC defect sites and emit as photons.

Figure 2B:
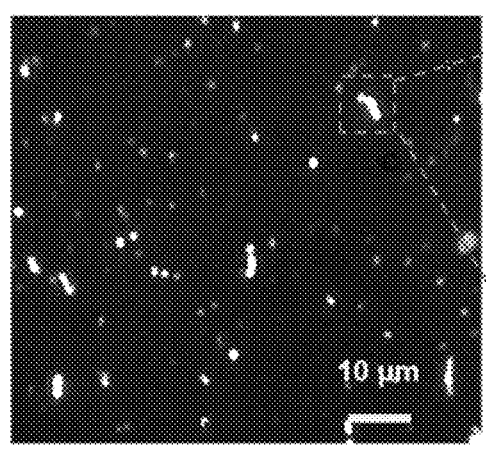

Hyperspectral fluorescence imaging using a custom-built microscope was also performed to investigate the defect PL at the individual OCC-SWCNT level. FIG. 2B shows a broadband (1100-1600 nm) PL image of the $C_6H_3(NO_2)_2$—OCC-tailored-SWCNT sample with a longpass filter at 1100 nm to filter out the pristine En PL emission. Hyperspectral imaging was then performed to resolve the spatial distribution of defects along the length of individual OCC-SWCNTs.

Figure 2C:
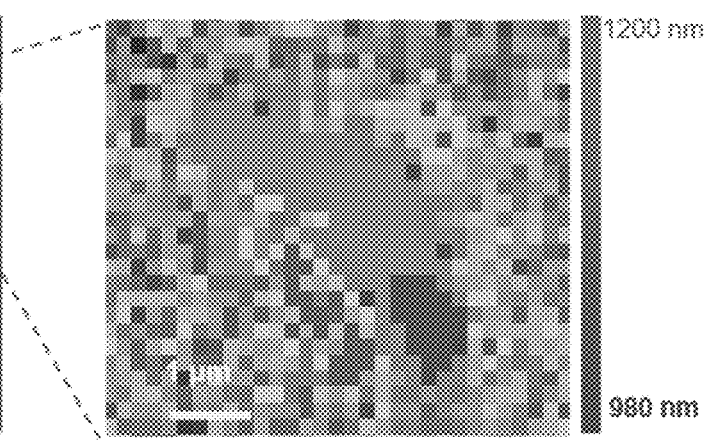

FIG. 2C shows the emission wavelength map of an individual, approximately 4 μm long $C_6H_3(NO_2)_2$—OCC-tailored-(6,5)-SWCNT, which features homogenous defect $E_{11}^-$ PL emission at approximately 1160 nm along the entire nanotube axis. This indicates uniform sidewall functionalization of the SWCNTs, presumably since the SWCNTs dispersed in superacid are bare (i.e., without surfactant), thus exposing the whole surface of the material and making it readily accessible to the reactant molecules.

Figure 3B:
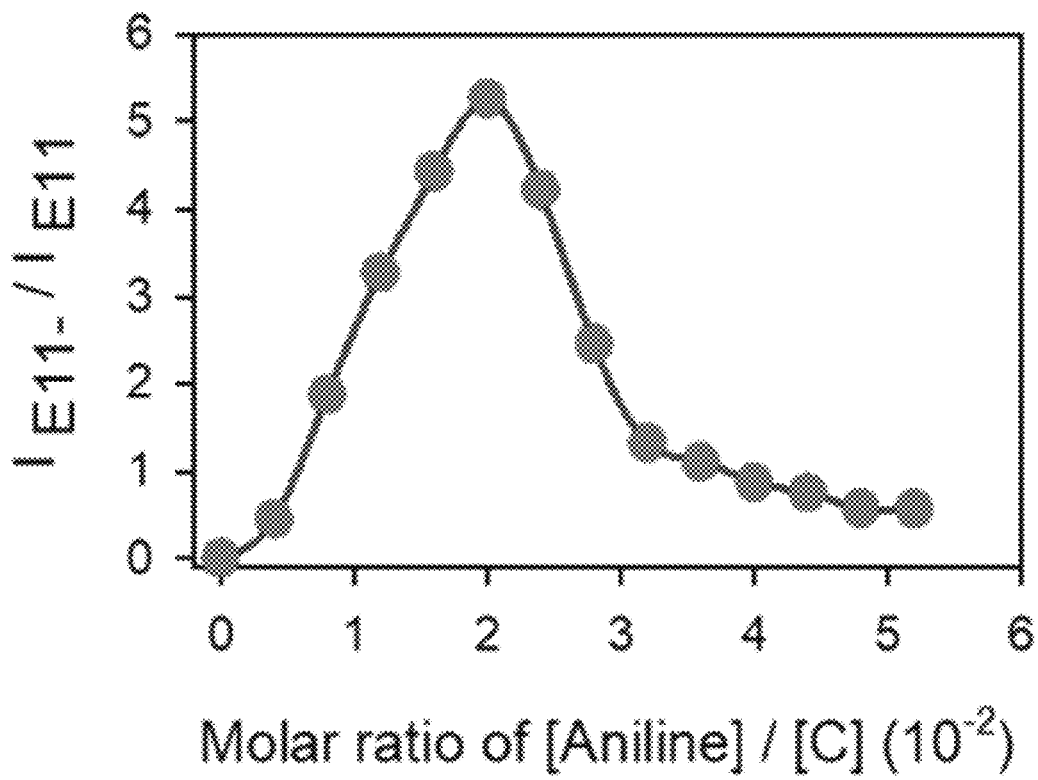
Figures 4A, 4B, 4C:
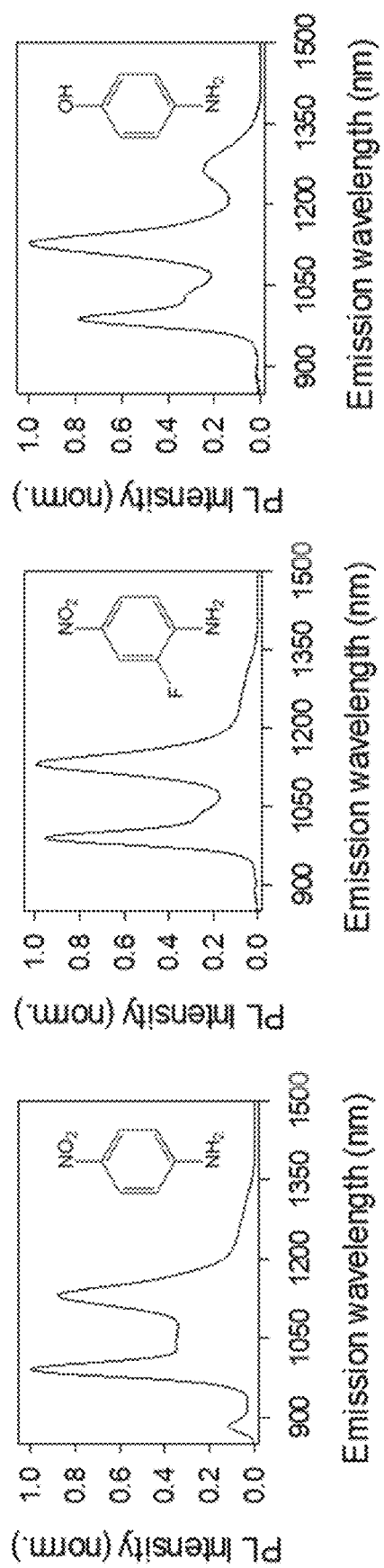
FIGS. 4A-4I. The PL spectra (at 565 nm excitation FIG. 3B.ion) of (6,5)-SWCNTs that are tailored with a wide variety of organic color centers from aniline derivatives.
Figures 4D, 4E, 4F:
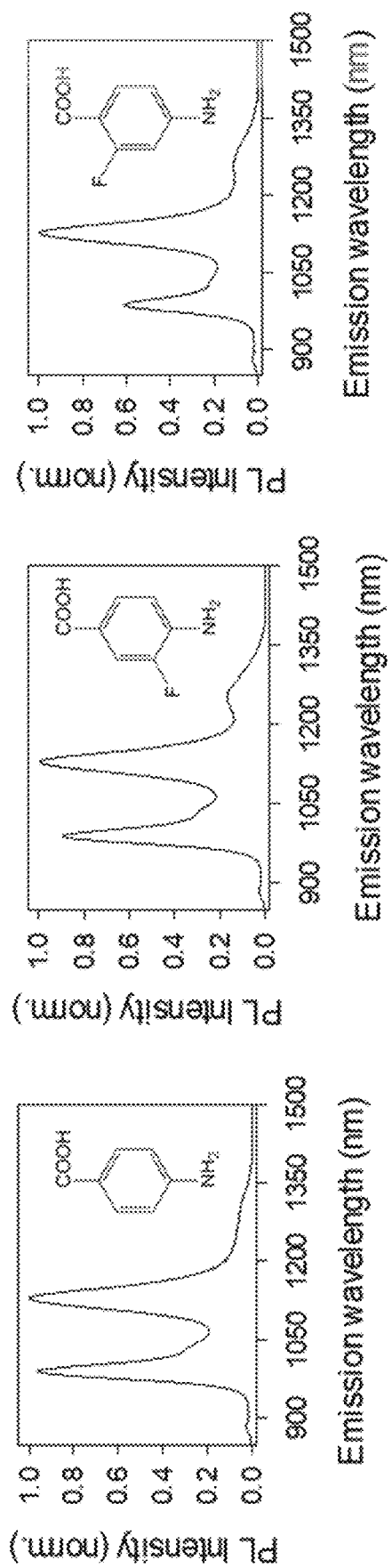
Figures 4G, 4H, 4I:
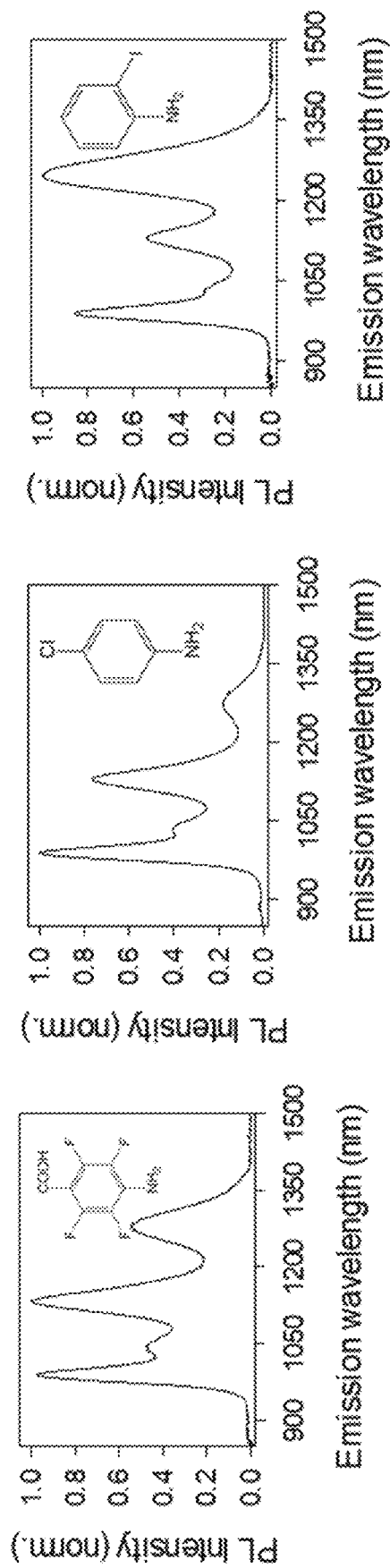

By controlling the relative amounts of reactants (3,5-dinitroaniline and SWCNTs), the functionalization degree and resulting PL intensity of $C_6H_3(NO_2)_2$—OCC-tailored-SWCNT can be easily controlled (FIG. 3B). The defect PL intensity of $C_6H_3(NO_2)_2$—OCC-tailored-SWCNT reaches its maximum at a reactant to carbon molar ratio ([aniline]: [C]) of approximately 1:50. Excessive reaction ultimately quenches both the PL of $E_{11}$ and $E_{11}^-$.

Because the optical behavior of an OCC is strongly dependent on the chemical nature of the defect (Piao, Y et al. 2013 *Nat. Chem.*, 5, 840-845; Kwon, H.; et al. 2016 *J. Am. Chem. Soc.*, 138, 6878-6885), the tunability of the functional group is particularly valuable for OCC chemistries. FIGS. 4A-I show the PL spectra of OCC-SWCNTs functionalized by a wide variety of aniline derivatives, including fluoroaniline and aminobenzoic acid derivatives, some of them (e.g., 2-fluoro-4-nitroaniline, 4-amino-2-fluorobenzoic acid, and 4-amino-2,3,5,6-tetrafluorobenzoic acid) have never been achieved in aqueous-based reactions due to the difficulty in synthesizing the corresponding diazonium salts (Piao et al. 2013; Kwon et al. 2016) demonstrating the versatility of this one-pot chemistry.

Figure 5A:
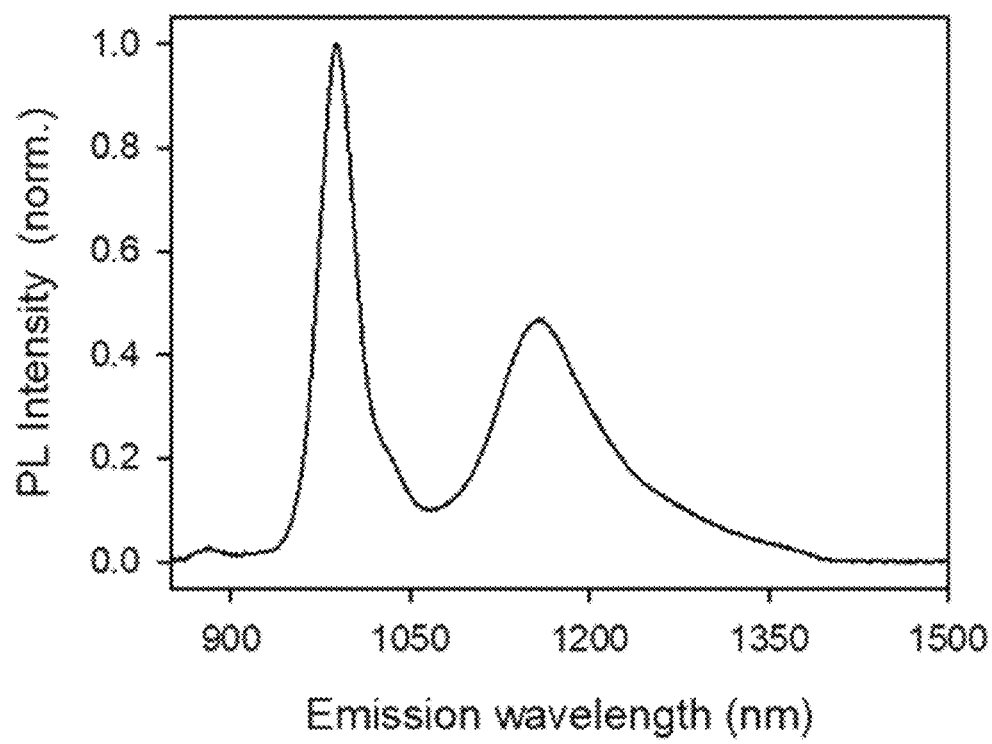
FIGS. 5A-5B.
Figure 5B:
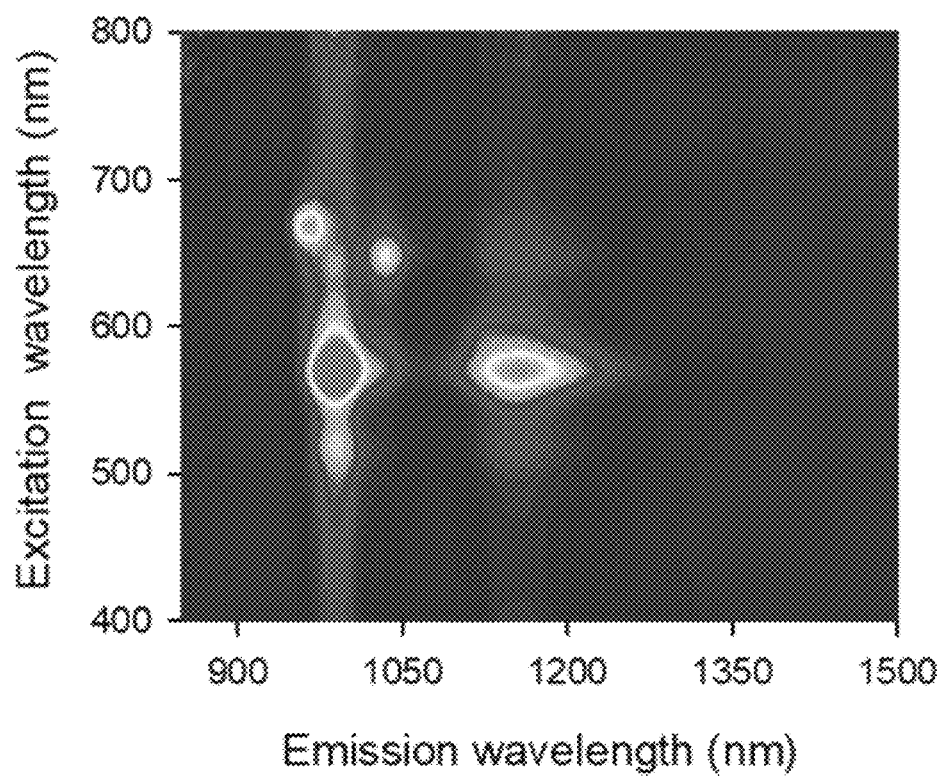
Figure 6A:
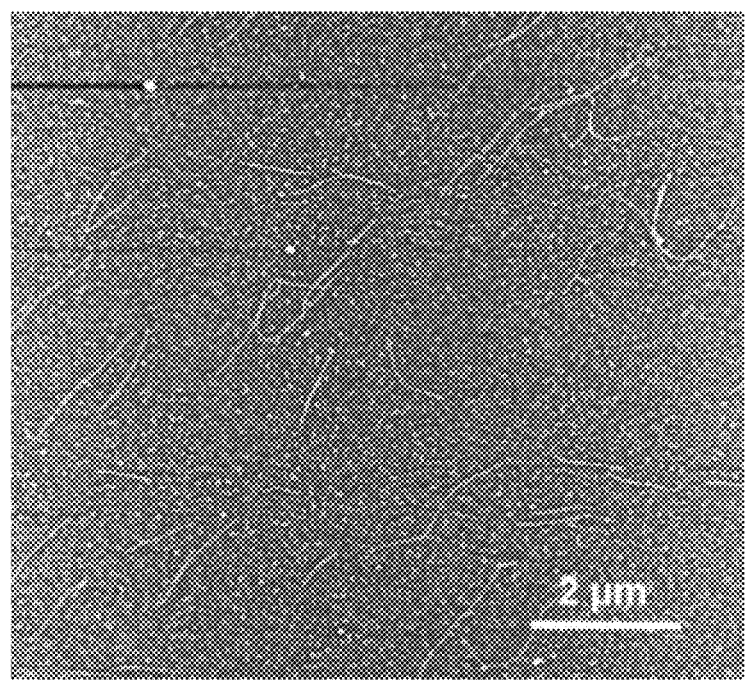
FIGS. 6A-6B.
Figure 6B:
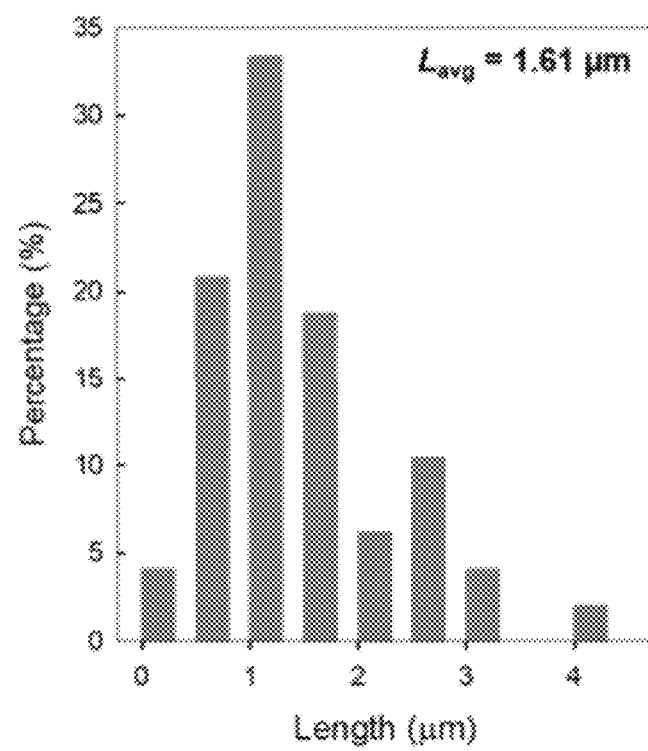
Figure 7A:
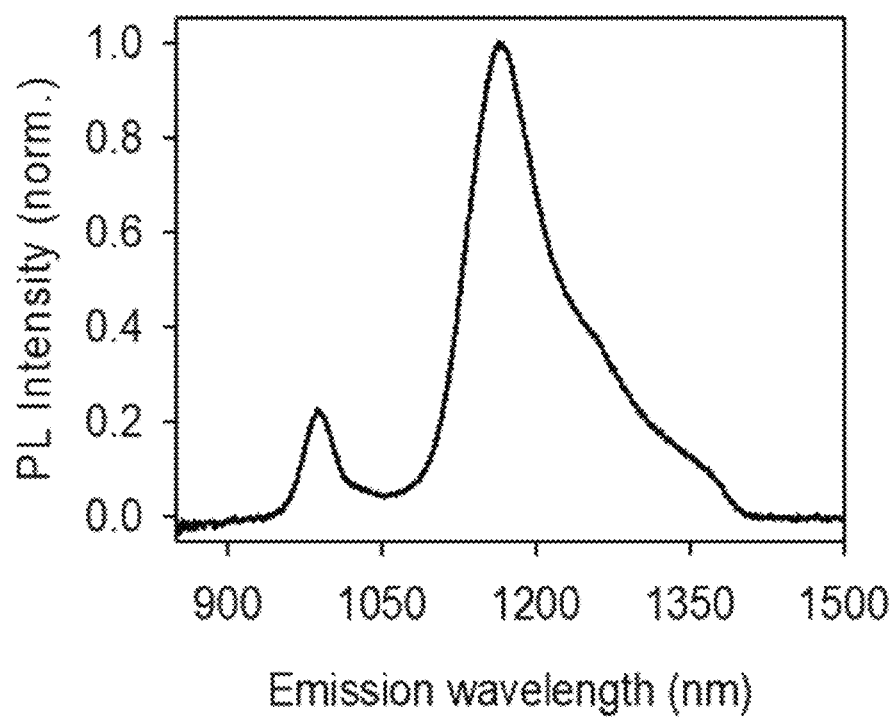
FIGS. 7A-7B.
Figure 7B:
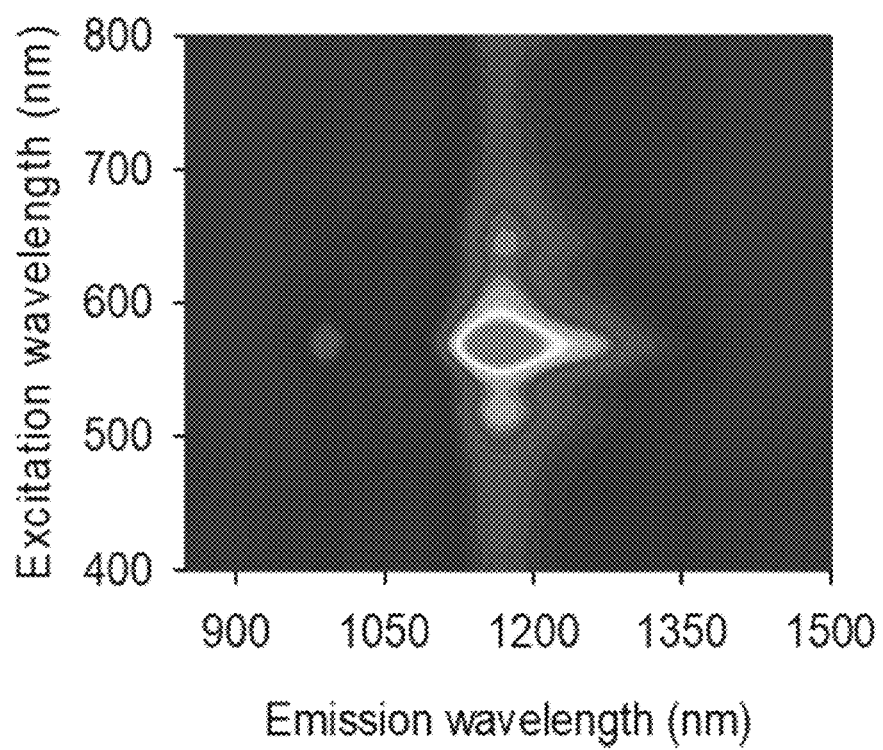
Figure 8A:
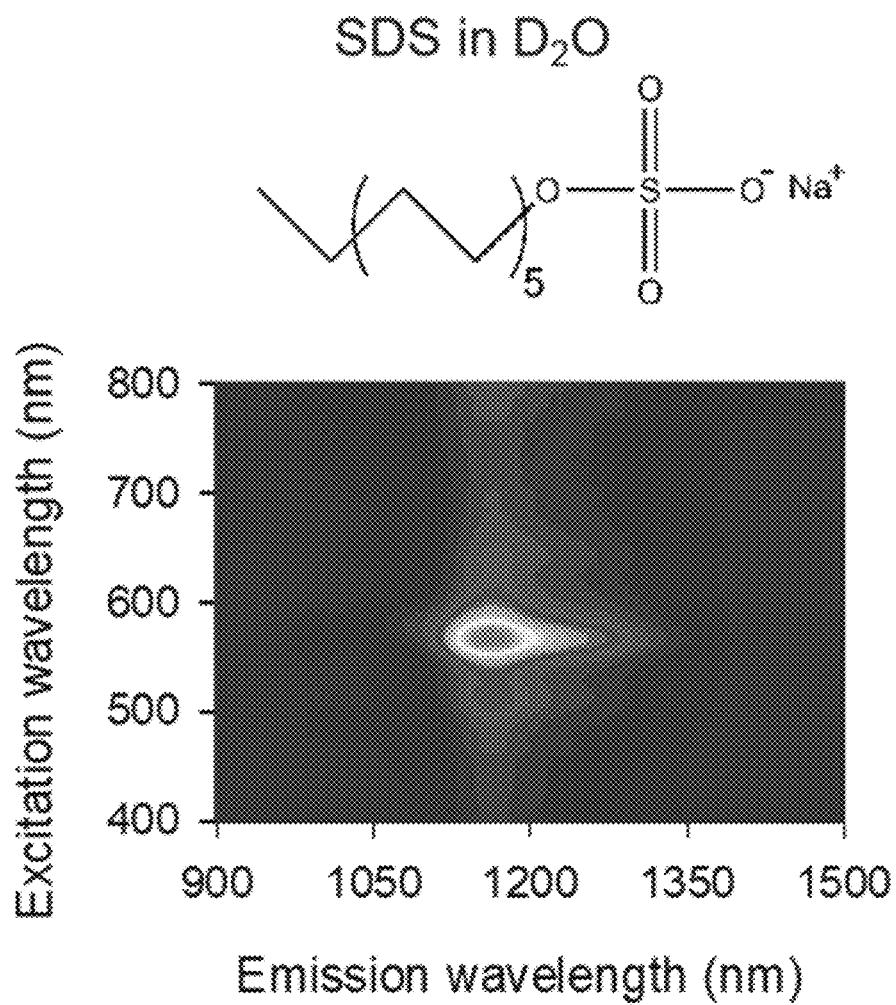
FIGS. 8A-8F. Individual OCC-SWCNTs encapsulated directly by various molecules and polymers. PL excitation-emission maps and spectra (565 nm excitation) of $C_6H_3(NO_2)_2$—OCC-tailored-SWCNTs that are directly dispersed in (FIG. 8A, FIG. 8B) 2 wt/v % SDS, (FIG. 8C, FIG. 8D) CTAB in $D_2O$, and (FIG. 8E, FIG. 8F) PFO-BPy in toluene.
Figure 8B:
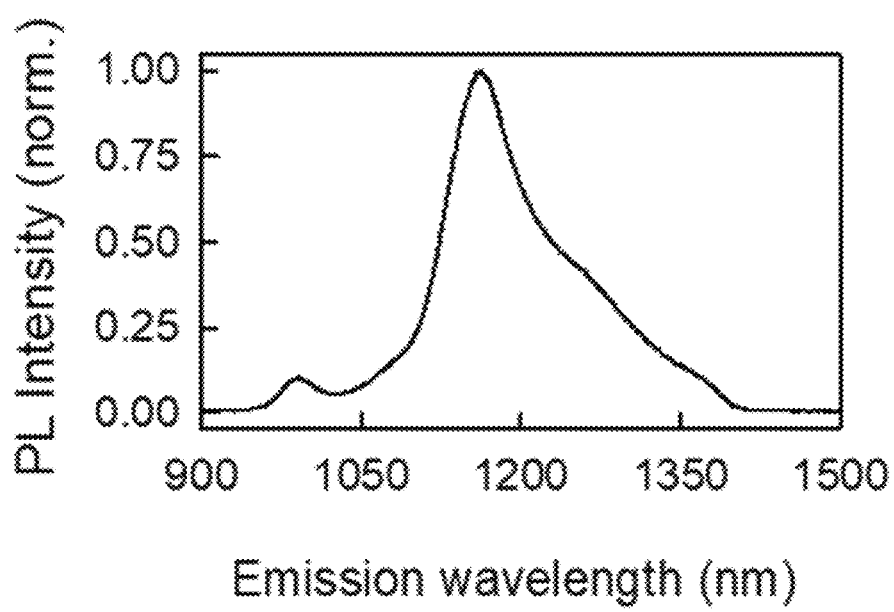
Figure 8C:
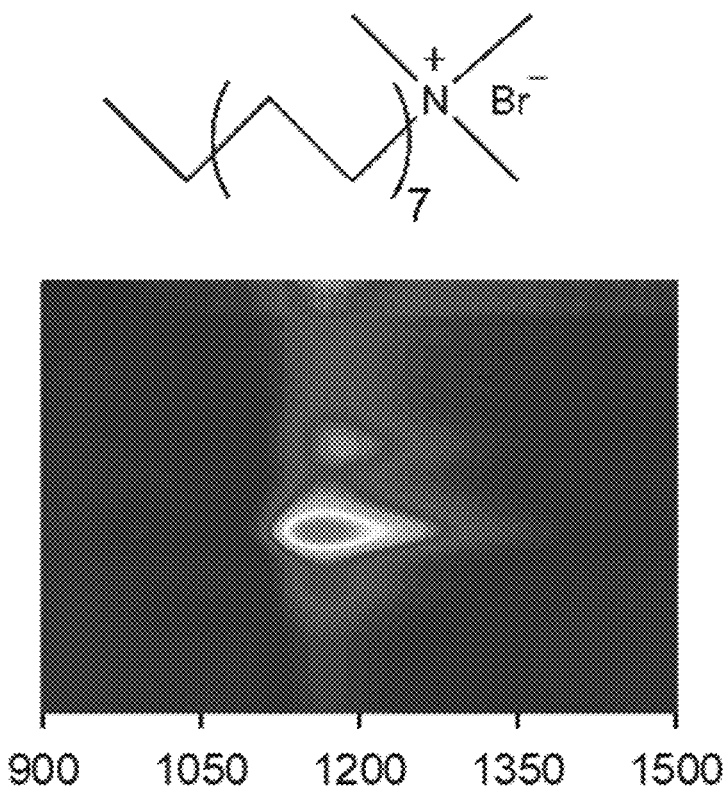
Figure 8D:
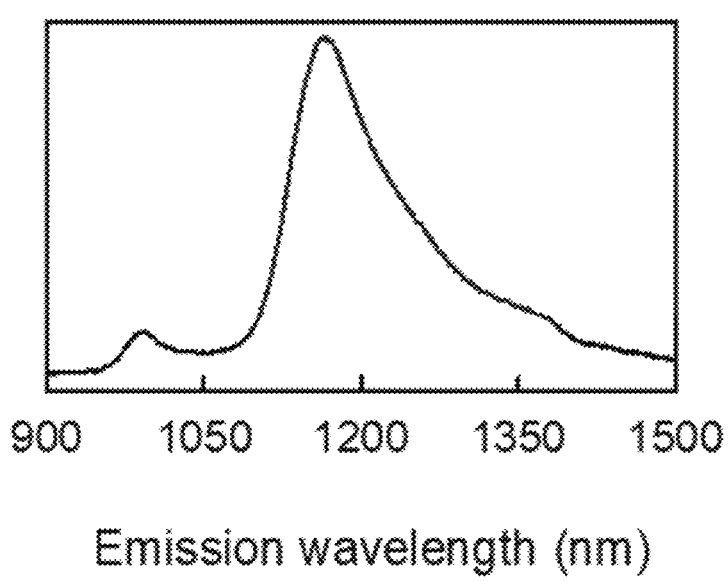
Figure 8E:
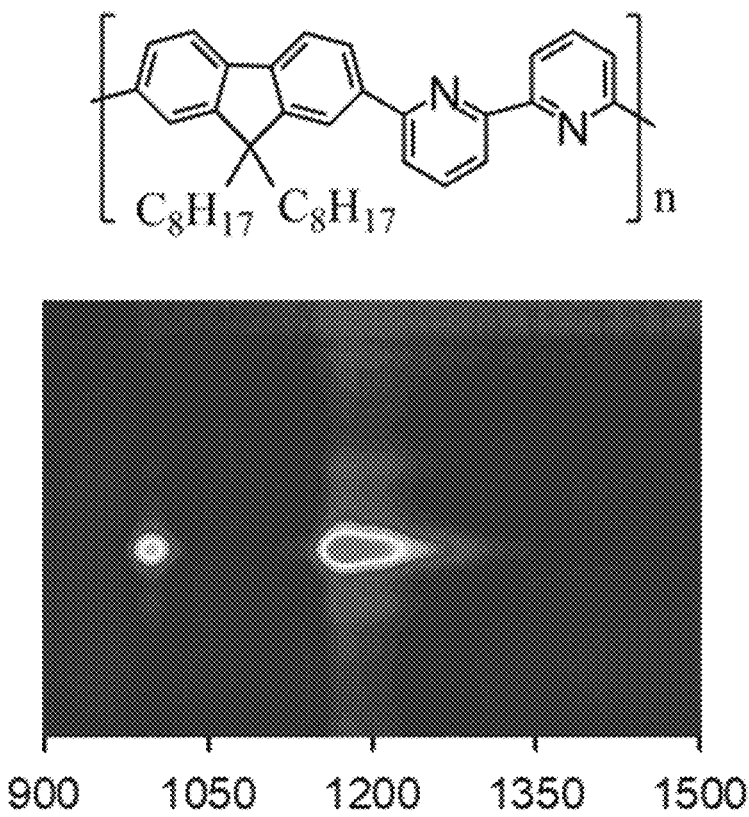
Figure 8F:
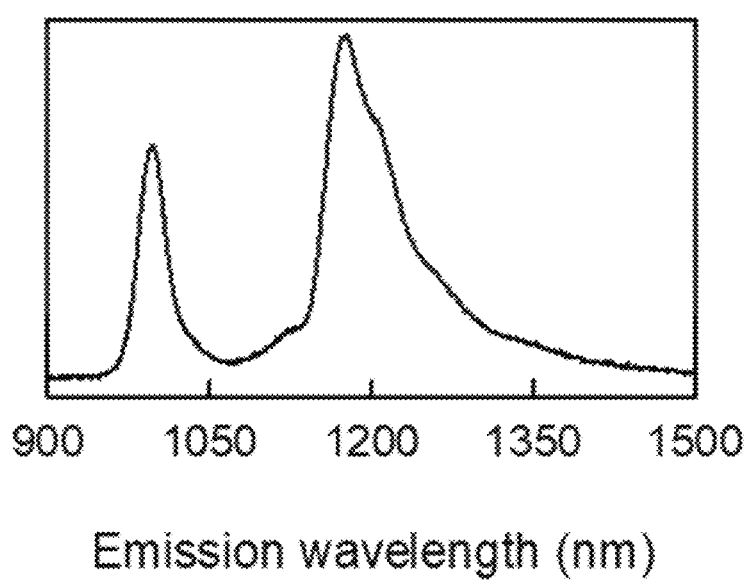

Further, long, individually-dispersed OCC-SWCNTs can be directly obtained by superacid-surfactant exchange (S2E) (Wang, P. et al. 2017 *ACS Nano* 11, 9231-9238; Wang, P. et al. 2018 *Small*, 14, 1802625) by simply adding the superacid-SWCNTs-reactants mixture into a DOC/NaOH solution. As the superacid is quenched by NaOH, the OCC-SWCNTs are instantly stabilized by the DOC surfactants as individual particles in water. The resulting OCC-SWCNTs exhibit much lower $E_{11}^-$ PL emission, when compared with that of water-quenched OCC-SWCNTs, (FIGS. 5A and 5B). This is possibly due to competition between the DOC surfactant and the reactant molecules in coating the exposed SWCNTs as the chlorosulfonic acid leaves. DOC coating of the nanotube surfaces will prevent the further attachment of aniline molecules to the carbon lattice. This problem was addressed by re-dissolving the water-quenched OCC-SWCNTs materials in the superacid and then performing S2E as a separate step. In this manner, OCC-SWCNTs were obtained with an average length of approximately 1.61 μm (FIGS. 6A and 6B) that exhibited much brighter $E_{11}^-$ PL (FIGS. 7A and 7B).

In addition to the scalability, another significant advantage of this synthetic route is that OCC-SWCNTs are produced as solid bulk materials, which we considered could be dissolved into a wide spectrum of solvents with different surfactants or polymers, depending on the specific requirements of subsequent processing steps necessary for different applications. For instance, in the case of biomedical imaging and therapy, surfactant molecules are typically highly toxic and cause biocompatibility concerns. Also, excess free surfactant molecules that are not physically adsorbed on the SWCNTs are difficult to remove from the solution, creating an obstacle to the further conjugation of SWCNTs with imaging labels or bioactive molecules. Although prolonged dialysis can be used to exchange bioincompatible surfactants (such as SDS) to other biocompatible and stable molecules, the method is time-consuming and the recovery yield is usually very low (<30%).

The resulting OCC-SWCNTs can be stabilized by a wide variety of surfactants and polymers, including SDS, cetrimonium bromide (CTAB) in $D_2O$, and poly[(9,9-dioctylfluorenyl-2,7-diyl)-alt-co-(6,6'-{2,2'-bipyridine})](PFO-BPy) in toluene, all of which exhibit bright defect PL (FIGS. 8A-8F). It is noteworthy that the PFO-BPy wrapped OCC-SWCNTs dispersed in toluene show $E_{11}^-$ emission with a much narrower full width at half maximum (FWHM) of ~63 meV compared with those dispersed in aqueous solution (~96 meV and ~103 meV for SDS and CTAB, respectively). This is possibly due to the absence of charge transfer from the nanotube OCCs to the nonpolar toluene solvent.

Single chirality SWCNTs possess characteristic optical absorption and emission because of their distinct electronic band structure. For single chirality OCC-SWCNTs, the unique optical properties include not only the native PL features of the nanotube host, but also the added defect PL, both of which are important to fully exploit the extraordinary PL properties for practical applications in optoelectronics. For example, single chirality OCC-SWCNTs are sought after as high-purity single-photon sources for quantum information processes.

Figure 9:
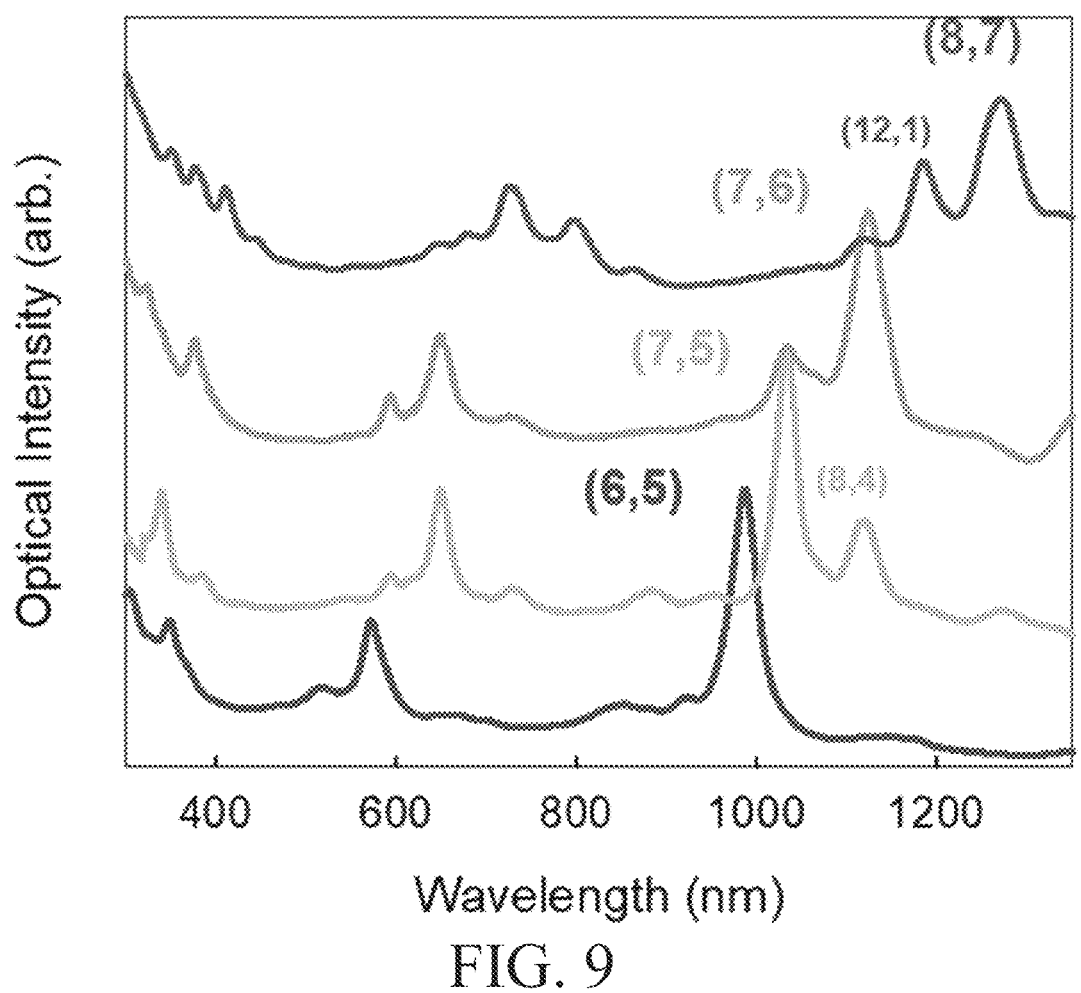
FIG. 9. UV-vis-NIR absorption spectra of ATPE-sorted $C_6H_3(NO_2)_2$—OCC-tailored-SWCNT.

The synthesized OCC-SWCNTs can be sorted to attain single chirality-enriched fractions at large volumes (FIG. 9). FIGS. 10A-10D shows four sorted solutions of $C_6H_3(NO_2)_2$—OCC-tailored-SWCNTs, including OCC-(6,5)-SWCNT, OCC-(7,5)-SWCNT, OCC-(7,6)-SWCNT, and OCC-(8,7)-SWCNT. The $C_6H_3(NO_2)_2$—OCC-tailored-(8,7)-SWCNT fraction also contained some OCC-(12,1)-SWCNT.

Figure 10E:
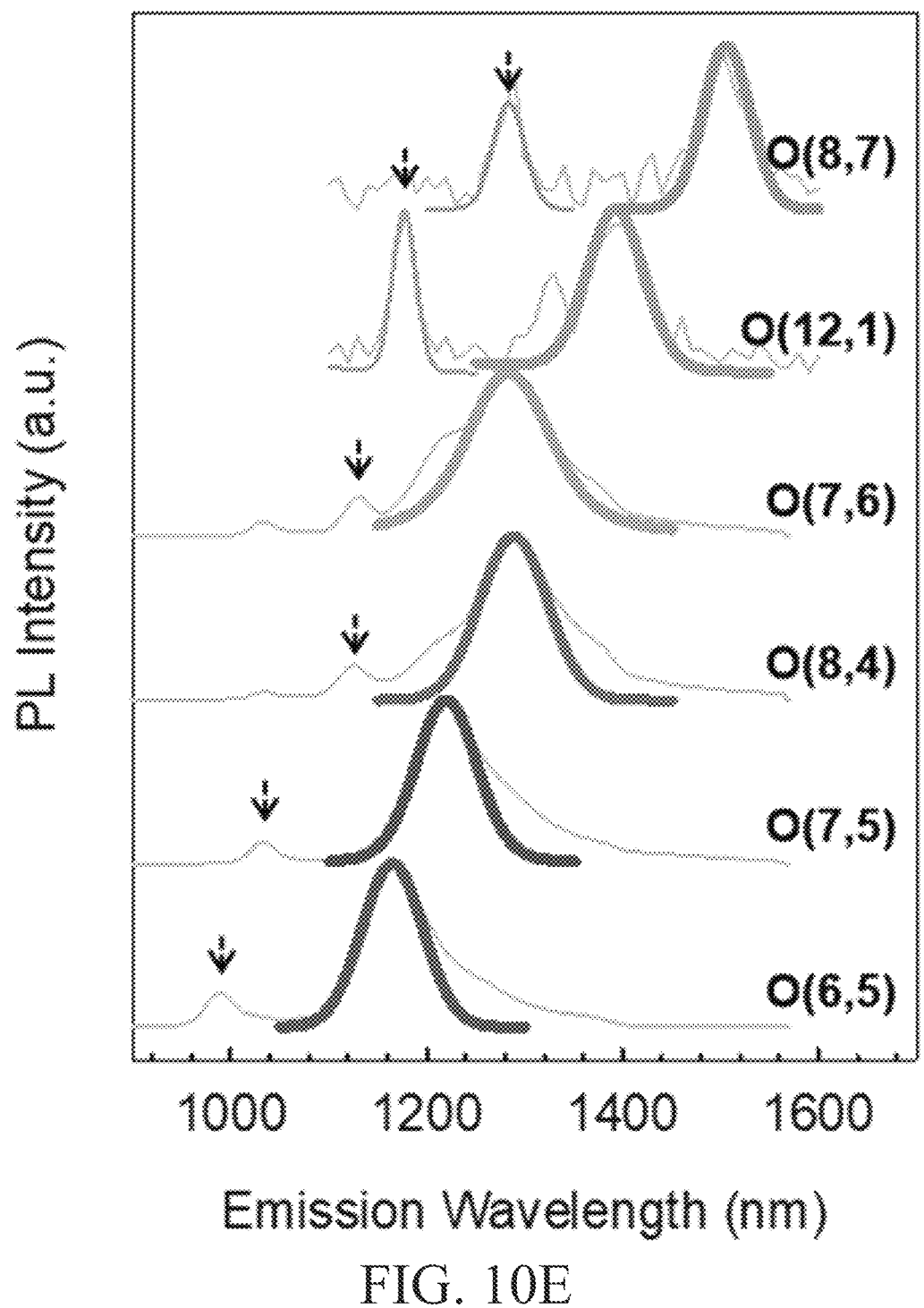

To avoid the strong water absorption at wavelengths greater than approximately 1350 nm, the $E_{11}^-$ peaks of the larger diameter $C_6H_3(NO_2)_2$—OCC-tailored (12,1)-SWCNT and (8,7)-SWCNT in solid-state were measured by hyperspectral imaging (FIGS. 11A-11D). It was observed that as the diameter of the host nanotube increased, the $E_{11}^-$ emission from the OCCs redshifted from approximately 1160 nm in the smallest (6,5) host to approximately 1510 nm in the largest (8,7) host (FIG. 10E). This diameter dependence is consistent with previous results and is due to the different depths of exciton traps for hosts of different diameters.

Figure 10F:
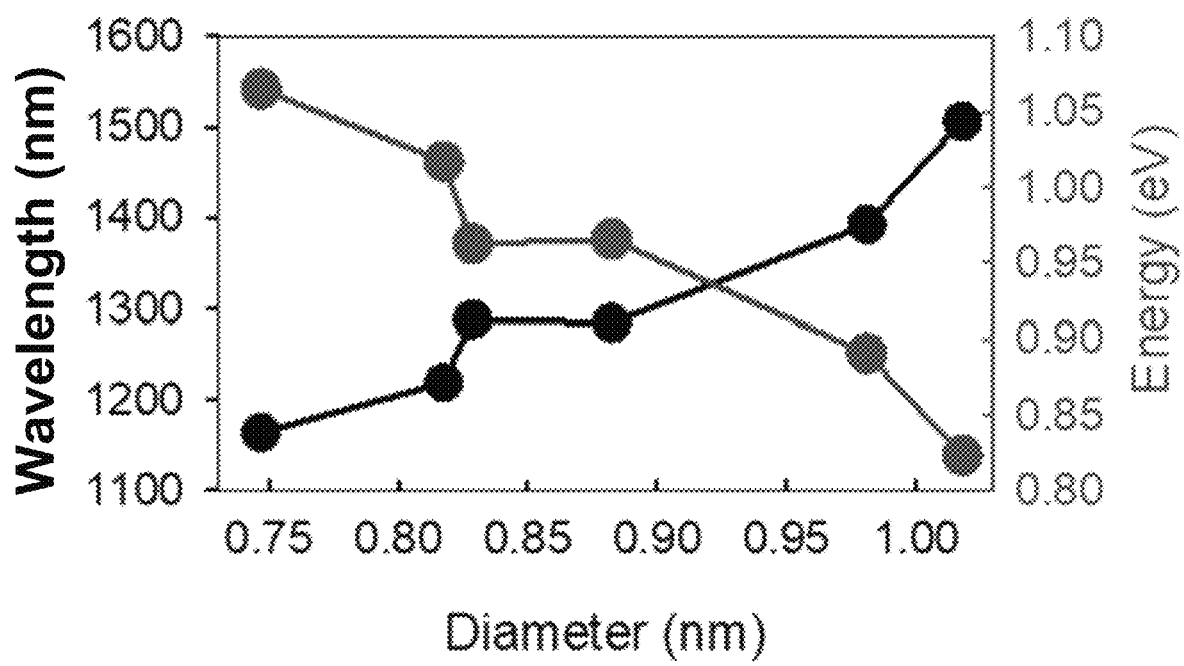
Figure 11B:
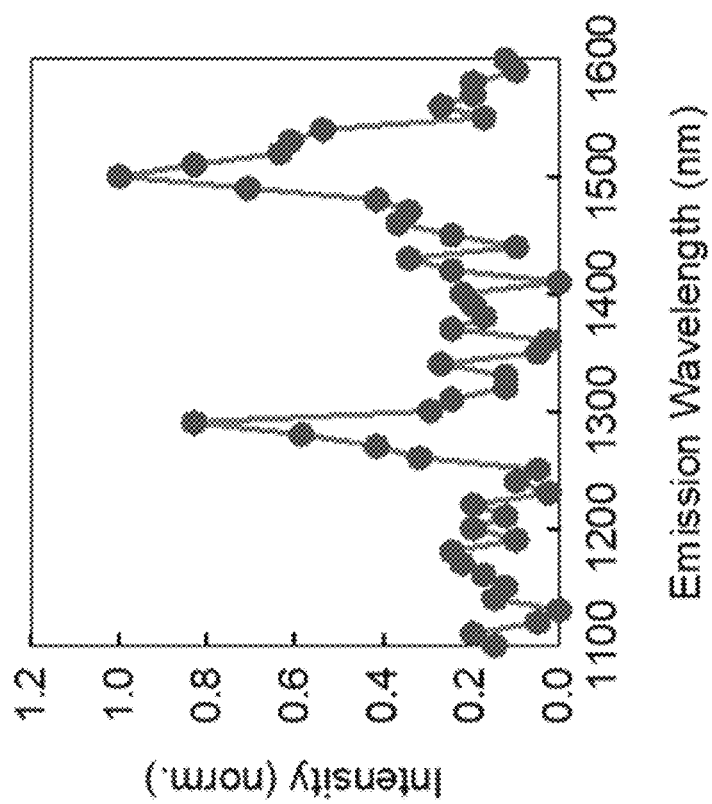
FIGS. 11A-11D. Hyperspectral PL images and corresponding PL emission spectra of $C_6H_3(NO_2)_2$—OCC-tailored-(8,7)-SWCNT (FIG. 11A, FIG. 11B) and $C_6H_3(NO_2)_2$—OCC-tailored-(12,1)-SWCNT (FIG. 11C, FIG. 11D).
Figure 11A:
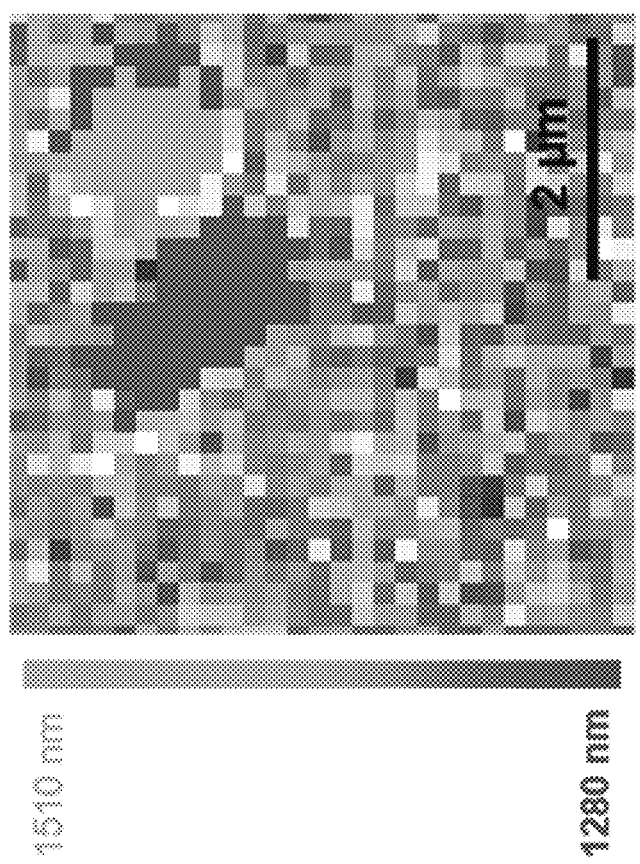
Figure 11D:
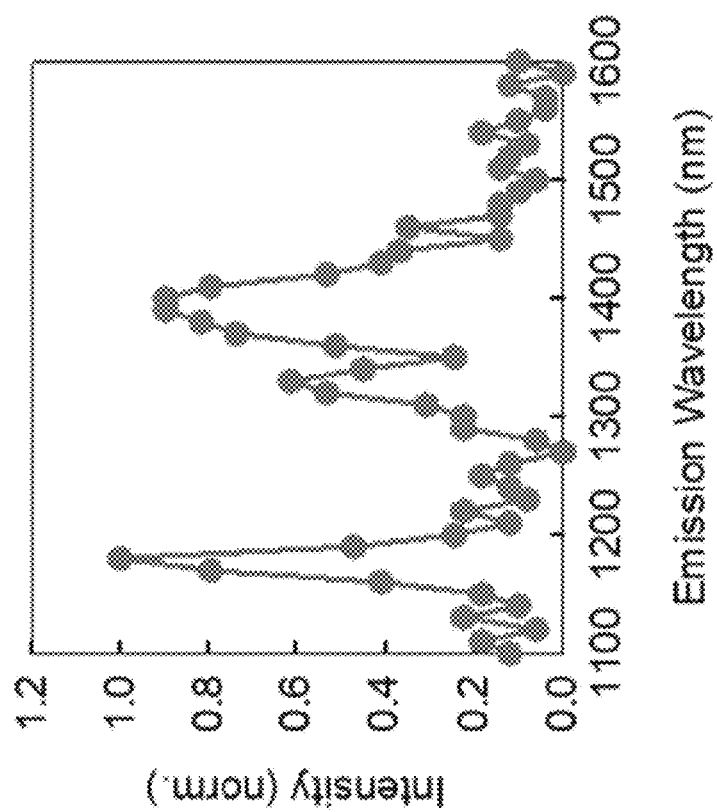
Figure 11C:
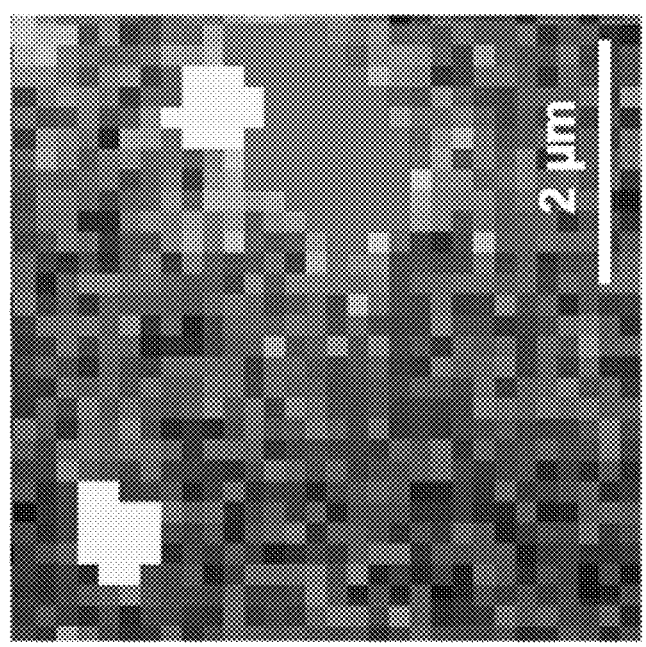
Figure 11C:

The general correlation between $E_{11}^-$ with the host nanotube diameter is further shown in FIG. 10F. Notably, the (8,7) chirality is one of the largest diameter (approximately 1.02 nm) SWCNTs ever reported as a host for OCCs, and the corresponding OCC-SWCNT sample features the most redshifted $E_{11}^-$ emission of approximately 1510 nm, which falls within the telecommunication range. This result is significant in that SWCNTs with large diameters are difficult to functionalize in an aqueous solution due to their relatively high structural stability and low reactivity. Therefore, this synthetic route also shows great potential for effectively functionalizing larger diameter SWCNTs and paves the way for fundamental studies and practical applications of OCCs in large diameter nanotube hosts.

Example 2

Synthesis of OCC-SWCNTs. Raw SWCNT materials, including CoMoCat SG65i (Sigma-Aldrich) and HiPco (Rice University, batch number 194.3), were used for this large-scale preparation process. The SWCNTs were dissolved in the superacid, chlorosulfonic acid (Sigma-Aldrich, 99.9%), at a concentration ranging from approximately 4 mg/mL with magnetic stirring, followed by the addition of an aniline derivative at different mole ratios relative to the SWCNT carbon, and equimolar amounts of sodium nitrite (Sigma Aldrich, ≥97.0%).

A wide variety of aniline derivatives were tested for these experiments, including 3,5-dinitroaniline (Sigma-Aldrich, 97%), 4-nitroaniline (Sigma-Aldrich, ≥99.0%), 4-aminobenzoic acid (ReagentPlus®, ≥99%), 2-fluoro-4-nitroaniline (Sigma-Aldrich, 95%), 4-amino-2-fluorobenzoic acid (Sigma-Aldrich, 97%), 4-amino-3-fluorobenzoic acid (Sigma-Aldrich, 97%), 4-amino-2,3,5,6-tetrafluorobenzoic acid (Sigma-Aldrich, 99%), 2-iodoaniline (Sigma-Aldrich, 98%), 4-chloroaniline (Sigma-Aldrich, 98%), and 4-aminophenol (Sigma-Aldrich, ≥98%).

The SWCNT-superacid mixture was added drop-by-drop into nanopure water with vigorous stirring, utilizing personal protective equipment, including goggles, a facial mask, lab coats, and acid-resistant gloves. This step should be performed in a fume hood. The resulting OCC-SWCNTs instantly precipitated out from the solution. The precipitates were then filtered on an Anodic Aluminum Oxide (AAO) filtration membrane with pore size of 0.02 µm (Whatman® Anodisc inorganic filter membrane), thoroughly rinsed with nanopure water, and then dried in a vacuum oven.

Example 3

Spectroscopic characterization. The OCC-SWCNTs were stabilized by 2 wt/v % sodium deoxycholate (DOC), sodium dodecyl sulfate (SDS) and cetrimonium bromide (CTAB) in $D_2O$ and 2 wt/v % poly[(9,9-dioctylfluorenyl-2,7-diyl)-alt-co-(6,6'-{2,2'-bipyridine})](PFO-BPy) in toluene for PL measurements. The OCC-SWCNTs were dispersed in 2 wt/v % DOC-$D_2O$ by tip ultrasonication with a power of 33 W and at 10° C. for 1 h, followed by centrifugation at 16400 rpm for 1 h (Eppendorf centrifuge 5810R) to remove undissolved bundles. The PL spectra and excitation-emission maps of the SWCNT solutions were collected using a HORIBA Jobin Yvon NanoLog spectrofluorometer, with a 450 W xenon arc lamp and a liquid-$N_2$ cooled InGaAs array. UV-vis-NIR absorption spectra were acquired through a PerkinElmer Lambda 1050 spectrophotometer equipped with a broad InGaAs detector. Raman spectroscopy measurements were performed on a HORIBA Jobin Yvon LabRAM Raman microscope, and the spectrum of each sample was the average data for three different regions.

Example 4

Sorting of OCC-SWCNTs. The ATPE method (Gui, H. et al. 2015 *Nano Lett.* 15, 1642-1646; Fagan, J. A. et al. 2014 *Adv. Mater.*, 26, 2800-2804; Khripin, C. Y. et al. 2013 *J. Am. Chem. Soc.*, 135, 6822-6825) was adapted and modified to separate OCC-SWCNTs with different chiralities. Specifically, 1-part of the OCC-SWCNT 2% (m/v) DOC solution was mixed with 0.3-parts of 20% (m/m) dextran (DX, MW 70000 Da, TCI) and 0.3-parts of 50% polyethylene glycol (PEG, MW 6000 Da, Alfa Aesar) aqueous solution to yield approximately 0.2-parts of OCC-SWCNTs concentrated in the bottom DX-enriched phase after mild centrifugation at 4000 g for 60 s. DOC surfactants were then gradually replaced by a sodium cholate (SC) and SDS co-surfactant system following the reported procedure so that the final concentration of SC and SDS were 0.9% (wt/wt) and 0.7% (wt/wt), respectively. The metallic/semiconducting SWCNT sorting process was then applied followed by diameter sorting until the desired chirality was enriched. The OCC-(6,5)-SWCNT, OCC-(7,5)-SWCNT, OCC-(7,6)-SWCNT and OCC-(8,4)-SWCNT were sorted from CoMoCAT SG65i, while the OCC-(8,7)-SWCNT and OCC-(12,1)-SWCNT were derived from the HiPco SWCNT starting material. The PEG and DX polymers were removed from the final semiconducting SWCNT-enriched solution by an ultrafiltration step using a centrifugal ultrafiltration nanotube (Amicon Ultra-15, PLHK Ultracel-PL membrane, 100 kDa) and the surfactants were changed to 2 wt/v % DOC in $D_2O$ solution.

Example 5

Individually dispersed, long OCC-SWCNTs. 10 mg of dried $C_6H_3(NO_2)_2$—OCC-tailored-SWCNT were fully dissolved in 50 mL chlorosulfonic acid (Sigma Aldrich, >99%) by magnetic stirring at 1200 rpm overnight. The OCC-SWCNT-superacid mixture was then added drop-by-drop into 0.75 M NaOH and approximately 0.08 wt/v % DOC (Sigma Aldrich, >97%) aqueous solution with vigorous stirring until the pH dropped to approximately 8. This neutralization is typically achieved by using 60 parts of 0.75 M NaOH-DOC for one part of OCC-SWCNT-superacid mixture. The solution was further stirred for 1 h followed by the addition of several drops of 1 M HCl aqueous solution to protonate the DOC molecules, causing them to coalesce into dark grey/black precipitates along with the SWCNTs. A 47 mm-sized polyvinylidene fluoride filtration membrane was used to filter and collect the precipitates. The dark grey/black precipitates were then mixed with nanopure water and a few drops of 1 M NaOH to tune the pH to approximately 7 to 8. The slurry was stirred for 3 days, and the resulting black solution was centrifuged at 16400 rpm for 60 mins (Eppendorf centrifuge 5810R) to remove undissolved SWCNT bundles.

We claim:

1. An organic color center (OCC)-tailored nanomaterial prepared by a method comprising:
   a) mixing-nanomaterials with an acid selected from chlorosulfonic acid and triflic acid, a nitrite salt, and one or more aniline derivative to produce a mixture; and
   b) adding the mixture to a reactive solvent to form the OCC-tailored-nanomaterial,
   wherein the nanomaterials are carbon nanomaterials or boron nitride nanomaterials, and
   wherein the one or more aniline derivative is 2-fluoro-4-nitroaniline, 4-amino-2-fluorobenzoic acid, 4-amino-2,3,5,6-tetrafluorobenzoic acid, 4-amino-3-fluorobenzoic acid, 4-amino-2,3-difluorophenol, 4-amino-3,5-difluorophenol, 2-amino-5-fluorophenol, 4,5-difluoro-2-methoxyaniline, 3,5-difluoro-2-methoxyaniline, 4-fluoro-2,3-dimethylaniline, 4-fluoro-3,5-dimethylaniline, 2-fluoro-4-methoxyaniline, 3-fluoro-2-methoxyaniline, 5-fluoro-2-methoxyaniline, or 2-fluoro-5-(trifluoromethoxy)aniline.

2. The OCC-tailored nanomaterial of claim 1, wherein the reactive solvent is ethanol.

3. The OCC-tailored nanomaterial of claim 1, wherein the reactive solvent is ethanol, propanol, butanol, pentanol, hexanol, ammonia, methylamine, ethylamine, diethylamine, phenol, their isotopic variants, or combinations thereof.

4. The OCC-tailored nanomaterial of claim 1, wherein the nanomaterials are single-walled carbon nanotubes, or double-walled carbon nanotubes.

5. The OCC-tailored nanomaterial of claim 1, wherein the acid is chlorosulfonic acid.

6. The OCC-tailored nanomaterial of claim 1, wherein the reactive solvent comprises $H_2O$, methanol, ethanol, propanol, butanol, pentanol, hexanol, ammonia, methylamine, ethylamine, diethylamine, phenol, their isotopic variants, or combinations thereof.

7. The OCC-tailored nanomaterial of claim 1, wherein the nitrite salt is $LiNO_2$.

8. The OCC-tailored nanomaterial of claim 1, wherein a concentration of nanomaterials dissolved in the acid is in a range from 1 μg/mL to 50,000 μg/mL.

9. The OCC-tailored nanomaterial of claim 1, wherein the nanomaterials are carbon nanomaterials.

10. The OCC-tailored nanomaterial of claim 1, wherein the one or more aniline derivative is 4-amino-2,3,5,6-tetrafluorobenzoic acid.

* * * * *